United States Patent
Park et al.

(10) Patent No.: US 7,297,759 B2
(45) Date of Patent: Nov. 20, 2007

(54) PEPTIDES FOR INCREASING TRANSFECTION EFFICIENCY

(75) Inventors: Jong-Gu Park, Daegu (KR); Ik-Jae Moon, Daegu (KR); Young-Cheol Kim, Daegu (KR)

(73) Assignee: Welgene, Inc., Daegu (KR)

( * ) Notice: Subject to any disclaimer, the term of this patent is extended or adjusted under 35 U.S.C. 154(b) by 0 days.

(21) Appl. No.: 10/353,522

(22) Filed: Jan. 28, 2003

(65) Prior Publication Data
US 2003/0216296 A1 Nov. 20, 2003

(30) Foreign Application Priority Data
Jan. 29, 2002 (KR) .................. 10-2002-0005203

(51) Int. Cl.
| C07K 2/00 | (2006.01) |
| C07K 4/00 | (2006.01) |
| C07K 7/00 | (2006.01) |
| C07K 14/00 | (2006.01) |
| C07H 21/04 | (2006.01) |
| C12N 15/00 | (2006.01) |
| A61K 9/127 | (2006.01) |

(52) U.S. Cl. .................. 530/300; 530/324; 530/326; 530/327; 530/328; 536/23.1; 435/320.1; 424/450

(58) Field of Classification Search ................ 530/327, 530/328, 326; 424/450
See application file for complete search history.

(56) References Cited

U.S. PATENT DOCUMENTS
5,804,604 A 9/1998 Frankel et al.

FOREIGN PATENT DOCUMENTS
| FR | 2 792 204 A1 | 10/2000 |
| WO | WO 98/40502 A1 | 9/1998 |
| WO | WO9840502 | 9/1998 |
| WO | WO 01/09312 A2 | 2/2001 |
| WO | WO0119393 | 3/2001 |
| WO | WO 01/91798 A2 | 12/2001 |
| WO | WO0248377 | 6/2002 |
| WO | WO 03/056013 A1 | 7/2003 |
| WO | WO 2004/048545 A2 | 6/2004 |

OTHER PUBLICATIONS

Pouton and Seymour, 2001, *Adv. Drug Deliv. Rev.*, 46:187-203.
Luo and Saltzman, 2000, *Nat. Biotech.*, 18:33-37.
Akhtar et al., 2000, *Adv. Drug Deliv. Rev.*, 44:3-21.
Lebedeva et al., 2000, *Eur. J. Pharm. Biopharm.*, 50:101-119.
Garcia-Chaumont et al., 2000, *Pharm. Therapeutics*, 87:255-277.
Juliano et al., 2001, *Mole. Intervention*, 1(1):40-53.
Hughes et al., 2001, *DDT*, 6(6):303-315.
Wang and Huang, 2000, *DDT*, 5(1):10-16.
During, 1997, *Adv. Drug Deliv. Rev.*, 27:83-94.
Han et al., 2001, *Bioconjugate Chem.*, 12:337-345.
Boussif et al., 1995, *Proc. Natl. Acad. Sci. USA*, 92:7297-7301.
Schwartz et al., 2000, *Curreun Opinion in Molecular Therapeutics*, 2(2):162-167.
Astriab-Fisher et al., 2000, *Biochem. Pharm.*, 60:83-90.
Friedler et al., 2000, *J. Bio. Chem.*, 275(31):23783-23789.
Futaki et al., 2001, *J. Bio. Chem.*, 276(8):5836-5840.
Suzuki et al., 2002, *J. Bio. Chem.*, 277(4):2437-2443.
Silhol et al., 2002, *Eur. J. Biochem.*, 269:494-501.
Fawell et al., 1994, *Proc. Natl. Acad. Sci. USA*, 91:664-668.
Farhood et al., 1995, *Anal. Biochem.*, 225:89-93.
Vives et al., 1997, *J. Bio. Chem.*, 272(25):16010-16017.
Schwarze et al., 1999, *Science*, 285(5433):1569-1572.
Tyagi et al., 2001, *J. Bio. Chem.*, 276(5):3254-3261.
Eguchi et al., 2001, *J. Bio. Chem.*, 276(28):26204-26210.
Embury et al., 2001, *Diabetes*, 50:1706-1713.
Morris et al., 2001, *Nature Biotech.*, 19:1173-1176.
Torchilin et al., 2001, *PNAS*, 98(15):8786-8791.
Zanta et al., 1999, *Proc. Natl. Acad. Sci. USA*, 96:91-96.
Ludtke et al., 1999, *J. Cell Sci.*, 112:2033-2041.
Duguid et al., 1998, *Biophysical J.*, 74:2802-2814.
Schwarze et al., 2000, *Trends in Cell Biology*, 10:290-295.
Snyder et al., 2001, *Current Opinion in Molecular Therapeutics*, 3(2):147-152.
Hughes et al., 1999, Chapter 19, *Methods in Enzymology*, Antisense Technology, Part A, General Methods, Methods of Delivery, and RNA Studies, 313: 342-359.
Cho et al., 2001, *Cytotechnology*, 37:23-30.
Futaki et al., 2001, *Bioconjugate Chemistry*, 12:1005-1011.
Srinivasakumar et al., 2000, *Journal of Virology*, 74(14):6659-6668.
Efthymiadis et al., 1998, *J. Bio. Chem.*, 273(3):1623-1628.
PUBMED Abstract PMID 8554596 & Huang et al., 1995, *Biochem. Biophys. Res. Commun.*, 217(3):761-768.
Colin et al., "Liposomes enhance delivery and expression of an RGD-oligolysine gene transfer vector in human tracheal cells," *Gene Therapy*, 5:1488-1498 (1998).

*Primary Examiner*—Nancy Vogel
(74) *Attorney, Agent, or Firm*—JHK Law; Joseph Hyosuk Kim

(57) ABSTRACT

The present application discloses a transfection effective carrier polypeptide comprising derivatives of HIV Tat peptide.

19 Claims, 14 Drawing Sheets

(TatC:DNA:DP =4:1:4)

(TatC:DNA:LFA=3:1:5)

WRT7/P2 cells (X200)

Serum (−)

Serum (+)

Liposome alone

Serum (−)

Serum (+)

Liposome alone

PEPTIDES FOR INCREASING TRANSFECTION EFFICIENCY

BACKGROUND OF THE INVENTION

1. Field of the Invention

This invention relates to peptides that increase the efficiency of gene delivery into cells and tissues and methods pertaining to the use of the peptides for delivering nucleic acids into cells or tissues. More specifically, this invention relates to amino acid sequences that mediate effective delivery of nucleic acids into cells and tissues and methods for delivering nucleic acids into cells or tissues using the peptides.

2. General Background and State of the Art

Recently, as the fields of gene therapy and molecular biology have developed rapidly, an urgent need has emerged to effectively deliver nucleic acids into cells or tissues. To be useful in gene therapy and antisense therapy as well as in vitro cell line experimentation, an effective amount of nucleic acids must be delivered into the target cells or tissue. At the same time, the nucleic acid delivery method should induce less immune response or cytotoxicity to the host. Also, availability of large-scale production of delivered materials, or vehicles, is important for the success of gene based therapy. Presently, gene delivery can be broadly divided into viral and non-viral delivery. For virus-mediated gene delivery, retrovirus, adenovirus, and adeno-associated virus and so on have been used for the transfer of nucleic acids into cells or tissues. Virus-mediated gene delivery has drawbacks including narrow range of cell infectivity, immune response to viruses, difficulty of large-scale production of viral vectors, etc. (Yibin Wang et al., DDT. 5(1), 2000; Joanne T. Douglas. et al., Science & medicine 44-52 (March/April), 1997).

For non-viral gene delivery, many different agents or methods such as liposomes, polymers, calcium phosphate, electroporation, and micro-injection have been used (Saghir Akhtar et al., Adv. Drug Deliv. Rev. 44:3-21; Irina Lebedeva et al., Eur. J. Pharm. Biopharm. 50:101-119, 2000; Ch. Garcia-Chaumont et al., Pharmacol. Ther. 76:151-161, 2000). Preparation of non-viral vectors is relatively easy such that large-scale production of vectors can be done to accommodate preclinical or clinical trials. Non-viral vectors are also known to induce less immune response to the vectors, allowing repeated administration of the vectors to the host. For these reasons, gene therapy using non-viral vectors has become popular (Colin W. Pouton et al., Adv. Drug Deliv. Rev. 46:187-20, 2001).

Among the non-viral vectors developed to date, liposomes are the most frequently used gene transfer vehicle and are available commercially. In order to take advantage of the negatively charged nature of cell surface, a large number of liposomes are cationic, or positively charged. Cationic liposomes, complexed with nucleic acids or DNA, electrostatically interact with the cell surface, and the complexes are then known to be endocytosed into the cell cytoplasm. Whereas cationic liposomes mediate gene delivery effectively into cells in vitro, gene delivery in an in vivo system is quite limited as compared to viral vectors. Furthermore, the efficiency of gene delivery using cationic liposomes is generally dependent on the size of nucleic acids, cell lines and so on, even in an in vitro system. In addition, increased amounts of nucleic acids are known to induce cytotoxicity to cells (Saghir Akhtar et al., Adv. Drug Deliv. Rev. 44:3-21, 2000: Irina Lebedeva et al., Eur. J. Pharm. Biopharm. 50:101-119, 2000).

Cationic polymers have been used to increase the efficiency of gene delivery into cells. By manipulating the number of positively charged amine group, they are able to bind strongly with nucleic acids, and also interact with the cell, so that the required amount of the polymers as compared to that of cationic liposomes can be reduced. However, cytotoxicity, and insolubility of cationic polymers in aqueous solutions should be resolved in order to be useful as an effective gene delivery vehicle (Dan Luo et al., Nat. biotech. 18:33-37; Saghir Akhtar et al., Adv. Drug Deliv. Rev. 44:3-21, 2000). Recently, a biodegradable polymer that dissolves well in water has been developed but no data is available regarding its safety in vivo (Sang-Oh Han et al., Bioconjugate Chem. 12:337-345, 2001; Otmane Boussif et al., Proc. Natl. Acd. Sci. 92:7297-7301, 1995).

The present invention was developed according to the above need for improvement of a nucleic acid delivery system. The present invention provides a gene delivery system that includes peptides that enhance nucleic acid uptake by cells. In addition, the present invention provides methods by which nucleic acids are delivered into cells or tissue using the above mentioned peptides.

SUMMARY OF THE INVENTION

To achieve the aforementioned purpose, present invention provides peptides whose amino acid sequence is as follows: (X)n-Arg-Lys-Lys-Arg-Arg-Gln-Arg-Arg-Arg-Pro-Pro-Gln-Cys-(X)n (SEQ ID NO: 1), wherein X represents Arg-Gly-Asp (RGD), and n represents an integer from 0 to 2. The present invention also provides methods by which nucleic acids are delivered into cells or tissues using the above peptides.

The present invention is directed to a transfection effective carrier polypeptide comprising parts $A_n$-B-$A_n$, wherein part B is 70% homologous to SEQ ID NO:2, and A represents Arg-Gly-Asp, and n represents a number from 0 to 2, wherein parts A and B are covalently linked. Part B of the polypeptide may be 80% homologous to SEQ ID NO:2. Further, the polypeptide may be about 8 to 30 amino acids in length, or about 10 to 20 amino acids in length. In particular, the polypeptide may be represented by SEQ ID NOS: 1, 2, 3 or 4.

The invention is also directed to a method of inserting at least one nucleic acid into a cell, comprising contacting the cell with a composition comprising the nucleic acid and the polypeptide described above. In the above-described method, the composition may further comprise a nucleic acid delivery carrier. The nucleic acid delivery carrier may be a cationic liposome. In one aspect of the invention, the composition may be mixed before contacting the cell. And the nucleic acid may be an oligonucleotide with a size range from 10 to 1000 bases. Further, the nucleic acid may be a plasmid vector. Preferably, the length of the vector may be about 2 to 50 kbp. Or, the nucleic acid may be a single stranded DNA having a length from about 300 to about 20,000 bases. In the above-described method, the cationic liposome may be lipofectamine™, lipofectin™, oligofectin™, DMRIE-CT™, lipofectamine plus™, and lipofectamine™ 2000, or DOTAP-DOPE, among others.

In the method of the invention, the ratio of polypeptide, nucleic acid and liposome may be about 1-10:1:1-10 (w/w/w). The liposome may be DOTAP-DOPE (1:1). Further, the ratio of polypeptide, nucleic acid and DOTAP:DOPE (1:1) may be about 3-5:1:3-6 (w/w/w). In one embodiment, the liposome may be lipofectamine. Furthermore, in the above-described method, the ratio of polypeptide, nucleic acid, and lipofectamine may be about 3-5:1:3-6 (w/w/w).

The invention is also directed to an in vitro transfection system comprising the Tat polypeptide described above and a cationic liposome, as well as a kit that incorporates a container that includes the transfection reagents and written directions on how to use the transfection reagent kit, which may be included in the form of labels on the container or separate sheets of paper or other writing substrate.

These and other objects of the invention will be more fully understood from the following description of the invention, the referenced drawings attached hereto and the claims appended hereto.

DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
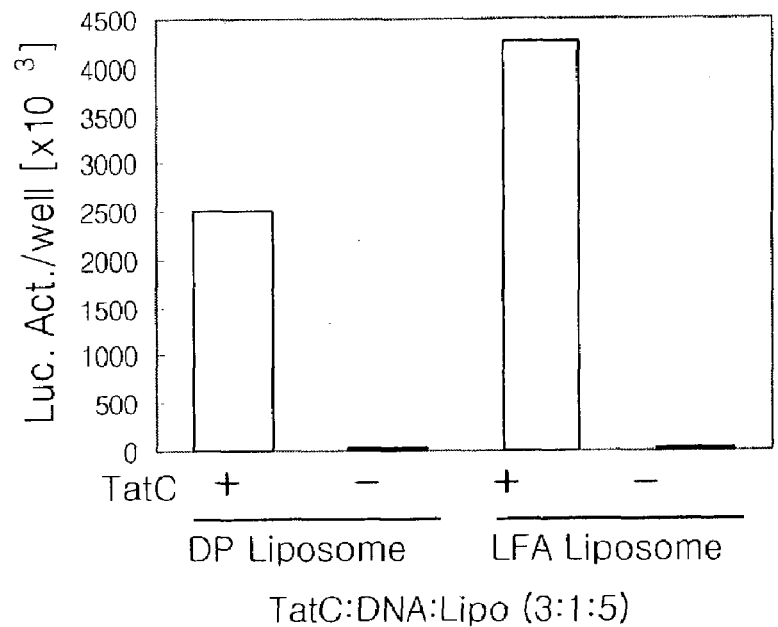
FIG. 1 shows luciferase activity using the triple complex of TatC peptide, DNA and cationic liposomes. +: Treatment of the triple complex of the TatC peptide/DNA/cationic liposome. -: Treatment of the dual complex of DNA/cationic liposomes (negative control).

In the present application, "a" and "an" are used to refer to both single and a plurality of objects.

As used herein, "about" or "substantially" generally provides leeway from being limited to an exact number. For example, as used in the context of the length of a polypeptide sequence, "about" or "substantially" indicates that the polypeptide is not to be limited to the recited number of amino acids. A few amino acids added to or subtracted from the amino acid sequence may be tolerated so long as its functional activity is retained. When mentioned with respect to a particular ratio of components, "about" or "approximately" provides leeway from being limited to an exact number, so long as the desired functional effect is achieved.

As used herein, administration "in combination with" or "complexed with" refers to one or more further agents includes simultaneous (concurrent) and consecutive administration or mixing in any order.

As used herein, "amino acid" and "amino acids" refer to all naturally occurring L-α-amino acids. This definition is meant to include norleucine, ornithine, and homocysteine.

Either single or three letter abbreviations for the amino acids are used throughout the application, and may be used interchangeably, and have the following meaning: A or Ala=alanine; R or Arg=arginine; N or Asn=asparagine; D or Asp=aspartic acid; C or Cys=cysteine; Q or Gln=glutamine; E or Glu=glutamic acid; G or Gly=glycine; H or His=histidine; I or Ile=isoleucine; L or Leu=leucine; K or Lys=lysine; M or Met=methionine; F or Phe=phenylalanine; P or Pro=proline; S or Ser=serine; T or Thr=threonine; W or Trp=tryptophan; Y or Tyr=tyrosine; and V or Val=valine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two ormore amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

In one aspect, the polypeptide variants of the present invention may contain any number of amino acids or alterations of amino acids in SEQ ID NO:2 of the transfection effective polypeptide, including substitutions and/or insertions and/or deletions, so long as the polypeptide variant includes a sequence that is at least about 70%, 75%, 80%, 85%, 90%, 95%, 96%, 97%, 98% or 99% identical to the polypeptide sequence represented by SEQ ID NO:2, and the presence of the variations do not hinder the transfection effective activity of the polypeptide.

As used herein, "Tat-derived peptides", "TatC peptide", "Tat polypeptide" or "Tat peptide" refers to a polypeptide that enhances transfection activity and contains an amino acid sequence that is at least about 70%, 75%, 80%, 85%, 90%, 95%, 96%, 97%, 98%, 99% or 100% identity to the polypeptide sequence represented by SEQ ID NO:2. In addition, the Tat-derived peptide may include insertions or deletions, and may be from 8 to 30 amino acids in length, and preferably may be 10 to 20 amino acids. It is understood that a polypeptide that is derived from Tat or TatC is not limited to the specific sequence of the Tat or TatC. It is understood that various mutations and conservative amino acid changes are tolerable, as well as certain non-conservative amino acid changes, so long as the polypeptide retains the ability to enhance transfection efficiency by addition thereby.

Applicants for the first time discovered that the inclusion of Tat peptide in a gene delivery system results in enhancement of transfection efficiency, and thus it would be within the purview of a person of skill in the art to make certain variations to the sequence, which retains the ability to enhance transfection efficiency.

As used herein, the tern "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in Current Protocols in Molecular Biology, John Wiley & Sons, N.Y. (1989), 6.31-6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

As used herein, "carriers" include pharmaceutically acceptable carriers, excipients, or stabilizers which are non-toxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "covalent derivatives" include modifications of a native polypeptide or a fragment thereof with an organic proteinaceous or non-proteinaceous derivatizing agent, and post-translational modifications. Covalent modifications are traditionally introduced by reacting targeted amino acid residues with an organic derivatizing agent that is capable of reacting with selected sides or terminal residues, or by harnessing mechanisms of post-translational modifications that function in selected recombinant host cells. Certain post-translational modifications are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl, tyrosine or threonyl residues, methylation of the α-amino groups of lysine, arginine, and histidine side chains (T. E. Creighton, Proteins: Structure and Molecular Properties, W. H. Freeman & Co., San Francisco, pp. 79-86 (1983)).

As used herein, "effective amount" is an amount sufficient to effect beneficial or desired clinical or biochemical results. An effective amount can be administered one or more times.

As used herein, "fragment" refers to a part of a polypeptide, which retains usable and functional characteristics. For example, as used within the context of the present invention, the polypeptide fragment has the function of enhancing transfection efficiency.

As used herein, "host cell" or "target cell" includes an individual cell or cell culture which can be or has been a recipient of a vector of this invention. Host or target cells include progeny of a single host or target cell, and the progeny may not necessarily be completely identical (in morphology or in total DNA complement) to the original parent cell due to natural, accidental, or deliberate mutation and/or change.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein, "purified" or "isolated" molecule refers to biological molecules that are removed from their natural environment and are isolated or separated and are free from other components with which they are naturally associated.

As used herein, "sequence identity", is defined as the percentage of amino acid residues in a candidate sequence that are identical with the amino acid residues in a native polypeptide sequence after aligning the sequences and introducing gaps, if necessary, to achieve the maximum percent sequence identity, and not considering any conservative substitutions as part of the sequence identity. The % sequence identity values are generated by the NCBI BLAST2.0 software as defined by Altschul et al., (1997), "Gapped BLAST and PSI-BLAST: a new generation of protein database search programs", Nucleic Acids Res., 25:3389-3402. The parameters are set to default values, with the exception of the Penalty for mismatch, which is set to −1.

As used herein, "subject" is a vertebrate, preferably a mammal, more preferably a human.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-associated virus (AAV)), DNA encapsulated in liposomes, DNA complexed with polylysine, complexed with synthetic polycationic molecules, complexed with compounds such as polyethylene glycol (PEG) to immunologically "mask" the molecule and/or increase half-life, or conjugated to a non-viral protein. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Tat Peptide

Peptides are made up of a string of amino acids whose size is usually less than one hundred amino acids. Some peptides, without any toxicity to cells, can reversibly bind to, condense nucleic acids, and can be effectively used to deliver them into cells or tissues.

Recently, as peptides consisting of generally basic amino acids were found to mediate intracellular transit of materials, intensive effort has been invested to develop a drug delivery system using these peptides. Peptides were derived from the HIV-1 Tat protein, SV 40 large T antigen, *Diosophila anntennapedia*, protamine sulfate, Histone H1 etc, of which a certain portion of the HIV Tat protein is shown to translocate proteins and genetic materials into cells. The HIV-1 Tat protein consists of 86 amino acid residues. The N-terminal 72 residues are encoded by exon 1 and the other residues by exon 2. A preferred region for its translocation activity resides in an amino acid sequence from the 49th to the 57th of the Tat protein (Eric Vives et al., J. Biol. Chem. 272(25):16010-16017, 1997).

In the present invention, inventors designed structurally and functionally effective Tat-derived peptides. In one embodiment of the invention, peptides containing a basic 12 amino acid sequence which plays a major role in DNA condensation and nuclear localization was derivatized. The inventors have exemplified different amino acids at the N-terminal and/or C-terminal ends of the above basic amino acid sequence of the peptide. The amino acid sequence of the mentioned peptides may be formulated as follows: (X)n-Arg-Lys-Lys-Arg-Arg-Gln-Arg-Arg-Arg-Pro-Pro-Gln-Cys-(X)n (SEQ ID NO: 1), wherein X represents Arg-Gly-Asp (RGD), and n represents an integer from 0 to 2. Sequences of exemplified Tat-derived peptides are shown in Table 1.

TABLE 1

| SEQ ID NOS | Peptides | Amino Acid Sequence | Length (mer) |
|---|---|---|---|
| SEQ ID NO:2 | TatC | RKKRRQRRRPPQC | 13 |
| SEQ ID NO:3 | RGD-TatC-RGD | RGDRKKRRQRRRPPQCRGD | 19 |
| SEQ ID NO:4 | TatC-RGD-RGD | RKKRRQRRRPPQCRGDRGD | 19 |
| SEQ ID NO:5 | Scrambled Tat (Sc-Tat) | RRKRQRKRRPQP | 12 |
| SEQ ID NO:6 | Tat | RKKRRQRRRPPQ | 12 |

In one aspect of the invention, gene delivery into cells or tissue is carried out by forming complex composed of target nucleic acid, Tat peptide, and nucleic acid delivery carrier.

Nucleic Acid

The nucleic acid to be inserted into the target cell may be DNA or RNA. The nucleic acid may be linear or circular, and may be in vector form or may be linear form without being associated with a DNA vector. The nucleic acid may be part of a virus or plasmid. In particular, the nucleic acid may be an antisense molecule. Accordingly, the nucleic acid may encode a therapeutic gene or may be a sequence that is complementary to a target gene so as to inhibit its expression.

In the present invention, the size or structure of nucleic acids does not affect the efficient delivery of nucleic acids, but a length of about 2 to 50 kbp of plasmid DNA is preferred. For oligonucleotides, a size of about 10 to 1000 bases is preferred for efficient gene delivery. For single stranded DNA, a length of about 300 to 20,000 bases is preferred for intracellular delivery.

In this invention, different reporter genes encoding luciferase, β-galactosidase, and green fluorescence protein were used for measuring peptide-mediated gene transfer into cells or tissues. FITC-labeled oligonucleotides were also used for the same purpose. The peptide-mediated gene delivery system according to the present invention may be broadly applied to many cells or tissues irrespective of type, or origin, but cancer cells or disease-related cells are preferred.

Nucleic Acid Delivery Carriers

The nucleic acid delivery carrier of the invention may include a variety of chemical compounds or methods that facilitate the delivery of the nucleic acid compounds of the invention into the cell of interest. A nucleic acid delivery method or carrier used in the invention may include but is not limited to cationic liposomes, PEG-lipid, PEG, poly-L-lysine, poly-D-lysine, dendrimer, Poly (D,L-lactic acid), virosomes, electroporation, magnetofection, naked DNA, lipid-polycation-DNA (LPD), folate-conjugated nanometric particles, cationic nanoparticle (NP) coupled to an integrin αvβ3-targeting ligand, (modified) virus coupled with DNA, short amphipathic peptide, a gene-activated matrix (GAM), poly(alpha-(4-aminobutyl)-L-glycolic acid) (PAGA), imidazole-containing polymers, chitosan, gelatin, atelocollagen, poly((D), (L)-lactic-co-glycolic acid) (PLGA), cyclodextrin based polymers, histidine and lysine (HK) polymer, glyco-targeted delivery systems, porous polymer microspheres, and the like.

When nucleic acids are sought to be delivered to a subject, the gene delivery system may include the nucleic acid, Tat polypeptide and a liposome in addition to suitable components for introduction into a subject. In a specific embodiment, it may be desirable to administer the pharmaceutical nucleic acid compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In yet another embodiment, the compound or composition may be delivered in a controlled release system. In one embodiment, a pump may be used. In another embodiment, polymeric materials may be used. In yet another embodiment, a controlled release system may be placed in proximity of the therapeutic target, i.e., the brain, thus requiring only a fraction of the systemic dose.

A composition is said to be "pharmacologically or physiologically acceptable" if its administration can be tolerated by a recipient animal and is otherwise suitable for administration to that animal. Such an agent is said to be administered in a "therapeutically effective amount" if the amount administered is physiologically significant. An agent is physiologically significant if its presence results in a detectable change in the physiology of a recipient patient.

In a preferred embodiment of the invention, liposoines are used. Liposomes may be used in combination with recognized carriers. The liposomes may include anionic, neutral and cationic liposomes. Cationic liposomes may include but not limited to lipofectin™, oligofectin™, DMRIE-C™, lipofectamine™, lipofectamine plus™, and lipofectamine™ 2000. Preferably, lipofectamine is used. Alternatively, a mixture of DOTAP:DOPE in about 1 to 1 ratio may be used. In particular, DOTAP:DOPE in about 1 to 1 ratio was shown to mediate efficient gene delivery into cells and tissues. Furthermore, it is contemplated that anionic liposomes or neutral liposomes may be used in the present invention as well.

Gene Delivery System

In a specific embodiment of the invention, nucleic acids to be transferred into cells or tissues are mixed with peptides and cationic liposomes, forming a complex, and then this complex may be mixed with targeted cells or tissues. The order of forming a triple complex, for example, with peptides, nucleic acids and cationic liposomes may be varied when desired. The complex may be formed in culture medium in the presence or absence of serum and antibiotics or in a buffer such as phosphate buffered saline. A preferred ratio of peptides, nucleic acids, and liposomes for the triple complex may be 1~10:1:1~10. In case of using lipofectamine or DOTAP/DOPE as cationic liposomes, the ratio of 3~5:1:3~6 of peptides:nucleic acids:liposomes is preferable.

In vitro Transfection System

The inventive in vitro transfection system comprises preferably a sterile solution of Tat peptide, nucleic acid delivery carrier and nucleic acid. The inventive transfection system is suitable for the transfection of a wide number of cell types with high efficiency and low toxicity. Transfection may be performed in the presence or absence of serum. It is preferable that the nucleic acid preparation contain the minimal amount of contaminant endotoxins.

In another embodiment of the invention, the transfection reagents are stored at +4° C. The pH of the storage solution may be in the range of about 5 to about 8. The quality of the DNA should be preferably of high quality. Preferably, $OD_{260}/OD_{280}$ ratio may be about 1.4 to about 1.8. Further, the nucleic acid should be sterile and free of any contaminant such as endotoxins.

Regarding cell density, at transfection, it is preferred that cell density (confluency) for most cell types be at about 50-90% at the time of transfection. It is preferred that the cells not be confluent or at stationary phase at the time of transfection. Furthermore, the optimal post-ion transfection incubation time may be determined and monitored using a reporter gene, which expresses an easily detectable protein such as but not limited to Luciferase, β-galactosidase or Green Fluorescent Protein.

The nucleic acid to be transfected may be an antisense oligonucleotide, a large circular antisense molecule, a plasmid or virus or any other nucleic acid. In one aspect, high transfection efficiency of the gene expression vector may depend on the promoter under which the gene of interest is expressed and the cell line used. For instance, cytomegalovirus (CMV) promoter is best known for high gene expression in a wide variety of cell lines. In other aspects, simian virus (SV40) and Rous sarcoma virus (RSV) promoters may also be preferable.

The amount of the Tat polypeptide and the nucleic acid delivery carrier used in the transfection system of the invention may depend on the amount of the nucleic acid to interact with the Tat polypeptide and the nucleic acid delivery carrier. For instance, the nucleic acid quantity may range from about 0.01 to about 50 µg for 100,000 cells.

In one aspect of the invention, the invention is directed to a kit that comprises a container that includes the inventive transfection reagent including the Tat polypeptide and nucleic acid delivery carrier such as a cationic liposome for use in carrying out in vitro transfection of cells.

The invention is also directed to a high through-put in vitro transfection system. In particular, the transfection system of the invention may contact target cells in multi-well plates such a 96-well plates, thereby effectuating multiple transfections simultaneously.

Gene Therapy

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode any protein of interest, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

Antisense Therapy

Antisense therapy includes specific binding of the linear or covalently closed antisense nucleic acid molecules that include an antisense segment for a target gene to inactivate or ablate target RNA sequences in vitro or in vivo. Antisense nucleic acid (DNA or RNA) and analogs thereof refers to a range of chemical species having a range of nucleotide base sequences that recognize polynucleotide target sequences or sequence portions through hydrogen bonding interactions with the nucleotide bases of the target sequences. The target sequences may be single- or double-stranded RNA, or single- or double-stranded DNA.

Such RNA or DNA analogs comprise but are not limited to 2'-O-alkyl sugar modifications, methylphosphonate, phosphorothioate, phosphorodithioate, formacetal, 3'-thioformacetal, sulfone, sulfamate, and nitroxide backbone modifications, amides, and analogs wherein the base moieties have been modified. In addition, analogs of molecules may be polymers in which the sugar moiety has been modified or replaced by another suitable moiety, resulting in polymers which include, but are not limited to, morpholino analogs and peptide nucleic acid (PNA) analogs. Such analogs include various combinations of the above-mentioned modifications involving linkage groups and/or structural modifications of the sugar or base for the purpose of improving RNaseH-mediated destruction of the targeted RNA, binding affinity, nuclease resistance, and or target specificity.

Therapeutic Composition

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (e.g., using slow release molecules by the intraperitoneal route or by using cells e.g. monocytes or dendrite cells sensitized ii vitro and adoptively transferred to the recipient). Depending on the route of administration, the peptide may be required to be coated in a material to protect it from the action of enzymes, acids and other natural conditions which may inactivate the ingredients.

For example, in the case of nucleic acids, the low lipophilicity of the antisense molecules will allow them to be destroyed in the gastrointestinal tract by enzymes capable of cleaving peptide bonds and in the stomach by acid hydrolysis. In order to administer the antisense molecules by other than parenteral administration, they will be coated by, or administered with, a material to prevent its inactivation. For example, antisense molecules may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, alumininum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the nucleic acid molecules are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Cell Cultures

K562 (chronic myelogenous leukemic cell line), HeLa (cervix adenocarcinoma), HeLaRC32 (cervix adenocarcinoma), MCF-7 (breast cancer), HL-60 (acute promyelocytic leukemic cell line), HepG2 (hepatoblastoma), Hep3B (liver carcinoma), A549 (lung carcinoma), NC1-H1299 (lung carcinoma), WI-38VA13 (normal lung), AGS (stomach adenocarcinoma), HT-29 (colon adenocarcinoma) were obtained from KCLB (Korea), and 293 (Human embryonic kidney cell) from Microbix, Inc. (Canada), and WRT7/P2 (monocyte/macrophage cell line) from Dr. Yagita (Junteno University, Japan). Cells used in this invention are listed in Table 2.

TABLE 2

| Cells | Specification | Purchaser |
| --- | --- | --- |
| K562 | Chronic myelogenous leukemia | Korean cell line bank (KCLB, Korea) |
| HeLa | Cervix adenocarcinoma | |
| HeLaRC32 | Cervix adenocarcinoma | |

TABLE 2-continued

| Cells | Specification | Purchaser |
| --- | --- | --- |
| HL-60 | Acute promyelocytic leukemia | |
| HT-29 | Colon adenocarcinoma | |
| MCF-7 | Breast cancer | |
| HepG2 | Hepatoblastoma | |
| Hep3B | Liver carcinoma | |
| A549 | Lung carcinoma | |
| NCI-H1299 | Lung carcinoma | |
| WI-38VA13 | Normal lung | |
| 293 | Human embryonic kidney cell | Microbix Inc., (Canada) |
| WRT7/P2 | Monocyte/macrophage cell | Dr. Yagita(Juntendo University, Japan) |

Cells were cultured in RPMI 1640 or EMEM (JBI, Korea) supplemented with 10% heat-inactivated Fetal Bovine Serum (FBS) (JBI or HyClone, USA), 2 mM L-Glutamine, penicillin (100 unit/ml) and streptomycin (100 ug/ml). Cells were maintained in a 5% $CO_2$ incubator at 37° C. Routine cell culture practices were strictly followed to maintain proper cell density, and culture media were exchanged a day before treating cells. Cultures were passaged at 70% confluence. Cell viability was examined on experiments using 0.4% trypan blue.

Example 2

Preparation of TatC Peptide, DNA and Cationic Liposome

Example 2.1

Preparation of Peptides

Peptides were prepared by solid phase on a peptide synthesizer from Anygen Inc.(Kwangju city, Korea). Peptides were purified by preparative HPLC and characterized by analytical HPLC and MALDI-TOF Mass analysis. Peptide sequences used in this invention are listed in Table 1. Peptides were stored frozen at −20° C. until further use.

Example 2.2

Preparation of Plasmid Vector DNA Containing Reporter Gene

In order to test transfection efficiency using the TatC peptide, the luciferase, LacZ (β-galactosidase) genes and GFP (Green Fluorescence Protein) were cloned into an expression plasmid vector. The luciferase gene was excised from pGEM-luciferase (Promega, USA) and cloned into the BaMH I-Xho I site of pcDNA3 (Invitrogen, USA). The LacZ (β-galactosidase) gene excised from pHook-2 LacZ (invitrogen, USA) was inserted into HindIII-BamHI-site of pcDNA3 (Invitrogen, USA). As for GFP expression, we used pEGFP-NI vector (5 kb, Clontech) as a GFP expression vector.

Example 2.3

Preparation of Cationic Liposomes

Lipofectamine (LFA), a commercially available cationic liposome, was purchased from Life Technologies (USA) and directly used in the present invention. DOTAP-DOPE, which is another combination of cationic liposomes, was prepared in house in a DOTAP-DOPE=1:1 complex (DP complex). To prepare the DP complex, 50 mg/ml of DOTAP (N-1(-(2,3-dioleoyloxy) propyl)-N,N,N-trimethylammoniumethyl sulphate; Avanti Polar Lipids, Inc. USA) in $CHCl_3$ and 50 mg/ml of DOPE (Dioleoylphosphatidylethanolamine, Avanti Polar Lipids, Inc. USA) in $CHCl_3$ were mixed in 1:1 ratio, and the complex was dried as a thin film using evaporator. The dried DP complex was then resuspended in 10 ml of 0.15M saline, by vortexing and sonication. Finally, crude DP complex formed by aforementioned procedure was passed through 100 nm of Mini-Extruder (Avanti Polar Lipids, Inc. USA, Alabaster) to obtain a DOTAP-DOPE complex of uniform quality.

Example 3

Formulation of Peptide/DNA/Cationic Liposome Complex (PDL System) and Enhanced Transfection Efficiency Example 3.1

Transfection Efficiency of the Triple Complex of the TatC Peptide/DNA/DP Liposomes In order to test transfection efficiency, the TatC peptide was precomplexed with the pcDNA3-luciferase vector DNA in 50 ul OPTI-MEM medium and was incubated for 5 minutes at room temperature. The DP liposomes was prepared in a 50 ul OPTI-MEM medium and added to the preformed complex of the TatC peptide and pcDNA3-luciferase vector DNA. The ratio of each component in the triple complex of the TatC peptide/DNA/DP liposomes was adjusted to 3:1:5 respectively. The triple complex of TatC peptide/DNA/DP liposomes was incubated for 10 minutes at room temperature and used for transfection into cells. After 5 hr incubation, 300 ul/well of the OPTI-MEM medium containing 20% Fetal Bovine Serum (FBS) was added into each transfection well. Further incubation for 16 hours was carried out before measuring transfection efficiency in luciferase activity using a luciferase assay kit (Promega, USA). To check luciferase activity of the pcDNA3-luciferase vector DNA, the following procedure was adopted. Cells were washed with PBS buffer (without $Mg^{2+}$ or $Ca^{2+}$) and lysed in 100 μl/well of 1×CCLR solution (Cell culture Lysis Reagent, 25 mM Tris-phosphate [pH 7.8], 2 mM DTT, 2 mM 1,2-diaminocyclohexane-N,N,N',N'-tetraacetic acid, 10% glycerol, 1% Triton X-100). Cell lysates was centrifuged at 12,000×g for 1 minute and 50 ul supernatant was carefully harvested without disturbing the cell pellet. The cell lysates then mixed with 20 μl Luciferase Assay reagent. Luciferase activity was tested using a luminometer (Berthold detection systems, Sirius, Germany). As a negative control, the DP liposomes alone. Result shown in FIG. 1 demonstrate that the triple complex of the TatC DNA/DP liposomes significantly enhances luciferase activity when compared to treatment liposomes alone. Hence, the triple complex of TatC peptide/DNA/DP liposomes can be effective carrier for DNA delivery.

Example 3.2

Transfection Efficiency of the TatC Peptide/DNA/LFA Liposome Complex

The TatC peptide/DNA (pcDNA3-luciferase vector)/LFA liposome complex was prepared as described in Example 3.1. Transfection was carried out according to the manufacturer's recommended protocol (Life Technologies, USA), and was tested for luciferase activity. FIG. 1 shows higher transfection activity with the TatC peptide/DNA/LFA liposome complex than with LFA liposomes only. Hence, the triple complex of the TatC peptide/DNA/LFA liposomes was shown to be an effective delivery system.

Example 4

Figure 2:
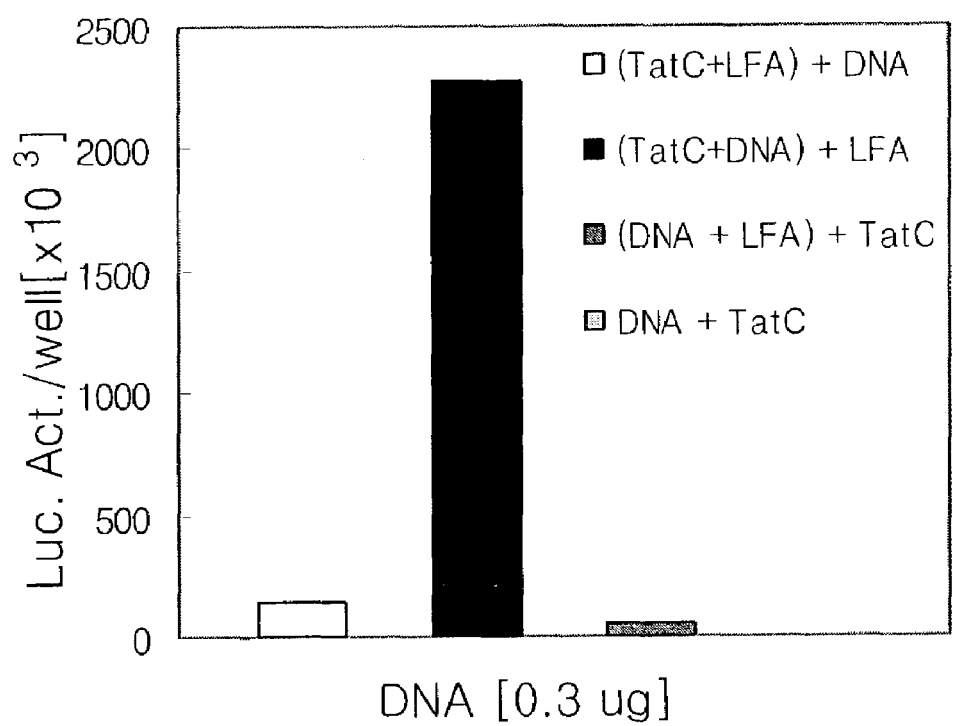
FIG. 2 shows comparison of transfection efficiency by mixing the order of addition of the components, TatC peptide, DNA, and cationic liposomes.

Transfection Efficiency of the Triple Complex of the TatC DNA/Cationic Liposomes, According to Mixing Order To deteremine if enhanced transfection efficiency could be attained, a TatC Peptide/DNA/cationic liposomes triple complex were formed by mixing them in different order. The mixing order of the triple complex of TatC peptide, DNA and cationic liposomes were as follows.
A: (Peptide+liposome)+DNA
B: (DNA+Peptide)+liposome
C: (DNA+liposome)+Peptide
D: DNA+liposome
Parentheses indicates the combination formed first. Luciferase assay was performed to examine transfection efficiency. When the TatC peptide and DNA were mixed first and then added with cationic liposome (LFA), transfection efficiency was shown to be highest as shown in FIG. 2. Thus the mixing order of (DNA+Peptide)+liposome appears to be significant for optimal transfection efficiency.

Example 5

Transfection Efficiency of the Triple Complex Relative to Mixing Ratios of the Tat C Peptide/DNA/Liposomes In order to test transfection efficiency of the triple complex, TatC peptide and liposomes (DP or LFA) were mixed with plasmid DNA in various ratios. The triple complexes were then transfected into K562 and HeLa cells. The plasmid DNA was a pcDNA3-luc vector with the luciferase gene. In detail, K562 cells were transfected with the triple complex in a ratio of DNA TatC peptide:liposomes, in a ratio of about 1:2~5:2~6 (w/w/w). In addition, the ratio of about 1:3~4:3~5 (w/w/w) were also used in HeLa cells. To compare the effects of the peptides of the present invention on gene delivery, liposomes alone were used as a control without the TatC peptide. Luciferase activity was then measured as described in Example 3.1.

Figure 3:
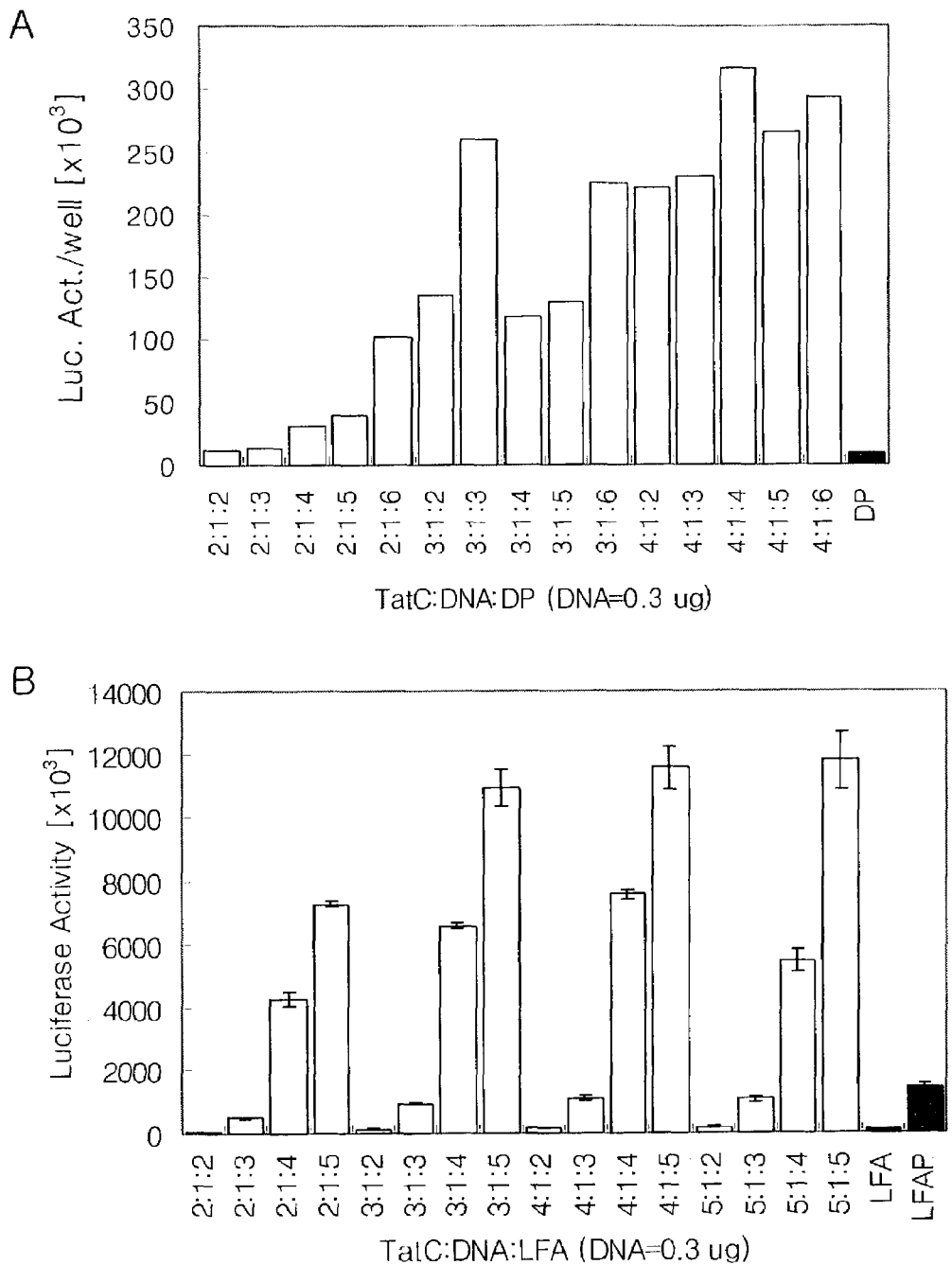
FIGS. 3A-3B show comparison of transfection efficiency in K562 cells, according to mixing ratios in forming the triple complex of TatC peptide, DNA, and cationic liposomes. A: Treatment of the triple complex of the TatC peptide/DNA/DP liposomes. B: Treatment of the triple of the TatC peptide/DNA/LFA liposomes.
Figure 4:
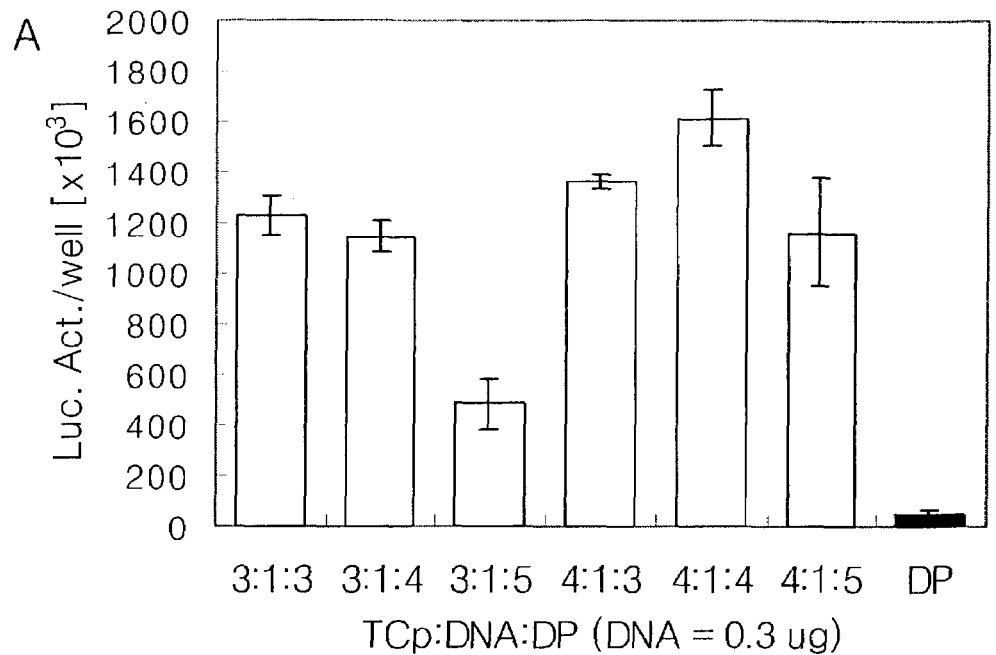
FIGS. 4A-4B show comparison of transfection efficiency in HeLa cells, according to mixing ratios in forming the triple complex of TatC peptide, DNA, and cationic liposomes. A: Treatment of the triple complex of the TatC peptide/DNA/DP liposomes. B: Treatment of the triple complex of the TatC peptide/DNA/LFA liposomes.
Figure 4:
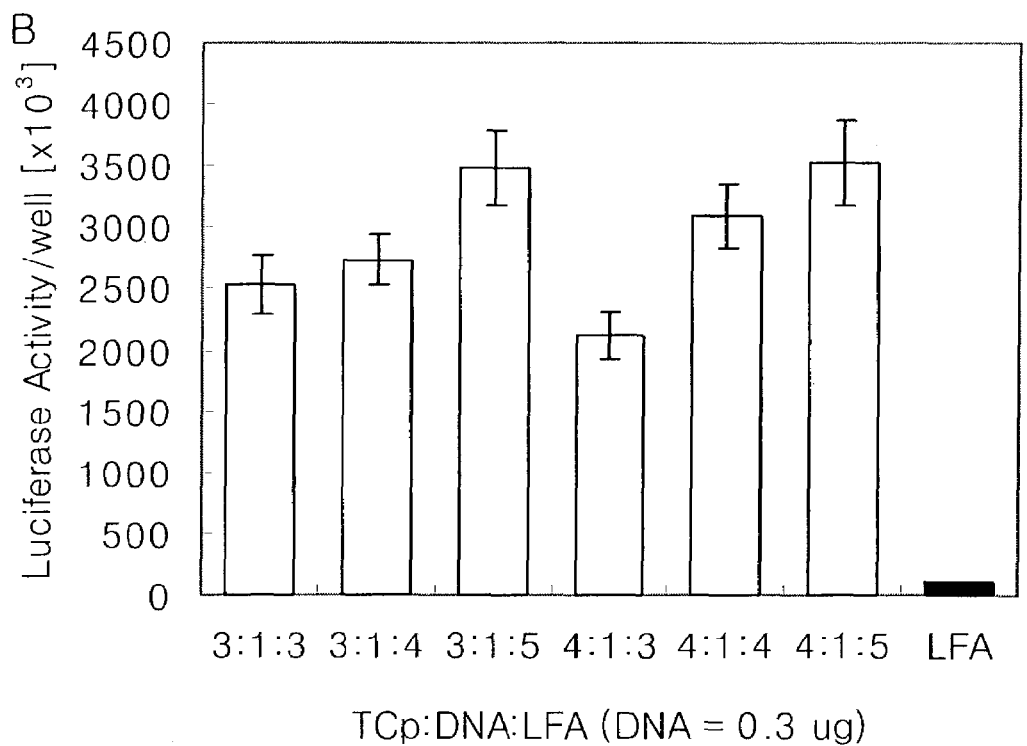

All combinations of the triple complex in K562 cells exhibited remarkably higher luciferase activities than the control (FIG. 3). In particular, higher activities were obtained as the amount of the complexed liposomes was increased in terms of higher weight ratio. DP liposomes showed high transfection efficiency when complexed with the peptide in a ratio of 3:3 or 4~6:4 (FIG. 3A), LFA liposomes showed high transfection efficiency in a ratio of 5~6:3~5 (FIG. 3B). Similar results were also obtained with HeLa cells (FIG. 4). In HeLa cells, while DP liposomes showed higher luciferase activity when complexed with the peptide in a ratio of 4:4 (FIG. 4A), LFA had high delivery efficiency in the ratio of 5:3~4 (FIG. 4B).

Example 6

Effect of pH on Transfection Efficiency of the Triple Complex of Peptide/DNA/Liposomes In order to test the effect of pH on transfection efficiency of the triple complex, buffers with differing pH in a range of pH 5.0 to 8.0 were employed with both PBS (phosphate-buffered saline) and the OPTI-MEM media (Life Technologies, USA). The buffers did not contain any serum or antibiotics. Buffers with pH 5.0 to 6.0 were prepared with PBS, and pH 6.5 to 8.0 buffer was prepared with OPTI-MEM (−). The triple complex of peptide/DNA/liposomes that was formed in the media buffer with differing pH were then added to HeLa cells. Luciferase activity was measured 24 hr after transfection. The cationic liposomes that were used were either DP liposomes or LFA. The triple complex was formed the peptide:pcDNA-luc. vector DNA: DP liposomes, at a ratio of about 3:1:3 (w/w/w). When LFA was used, a ratio of peptide:DNA: LFA was adjusted to about 3:1:5 (w/w/w).

Figure 5:
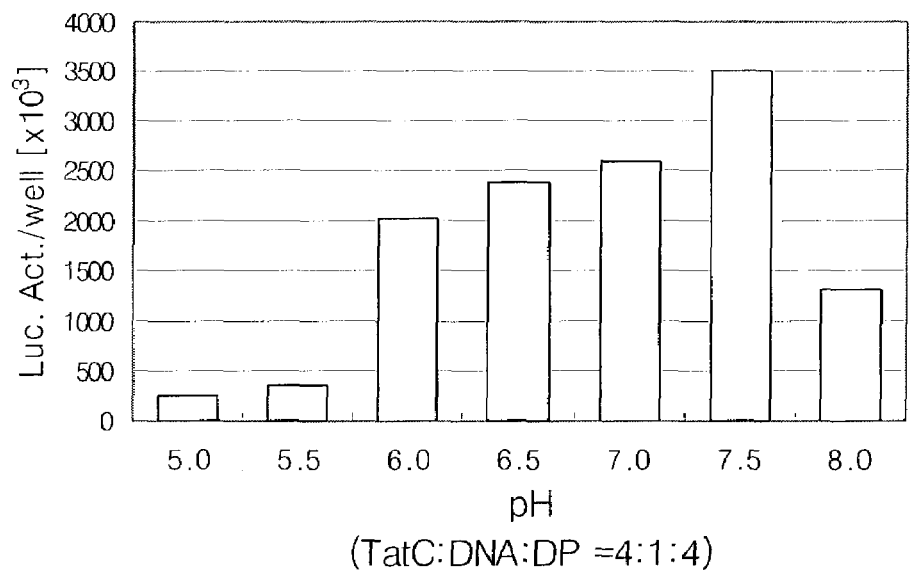
FIGS. 5A-5B show transfection efficiency in relation to pH during formation of the triple complex. A: Treatment of the triple complex of the TatC peptide/DNA/DP liposomes. B: Treatment of the triple complex of the TatC peptide/DNA/LFA liposomes
Figure 5:
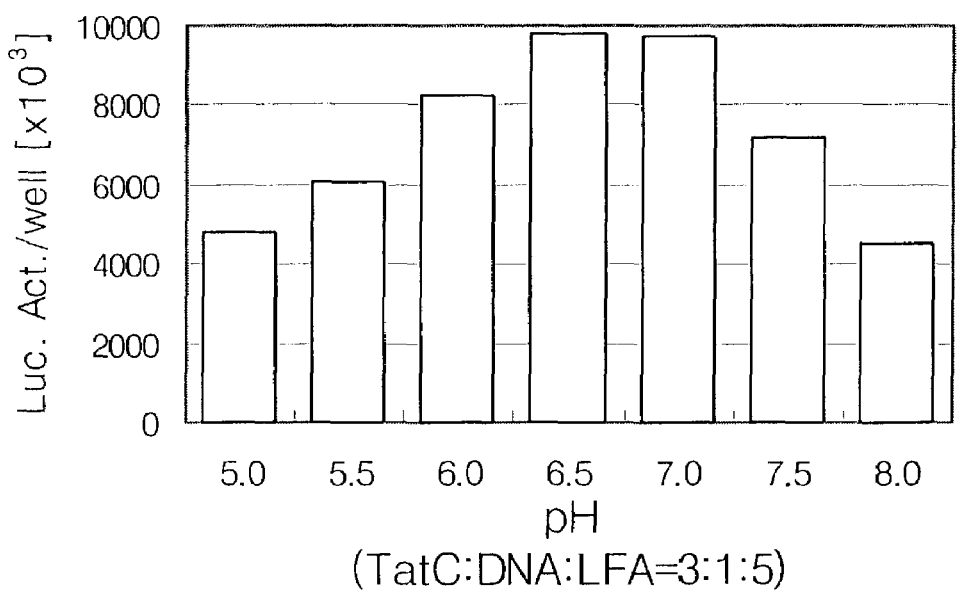

Luciferase activity was detected at most pH tested (FIG. 5). In particular, transfection efficiency was found to be higher in pH range of 6.0 to 7.5. These results indicate that strong acidic- or alkaline-conditions may influence the formation of the triple complex because these complexes are formed by electrostatic interaction among specific charges derived from peptide, DNA or liposomes.

Example 7

Figure 6:
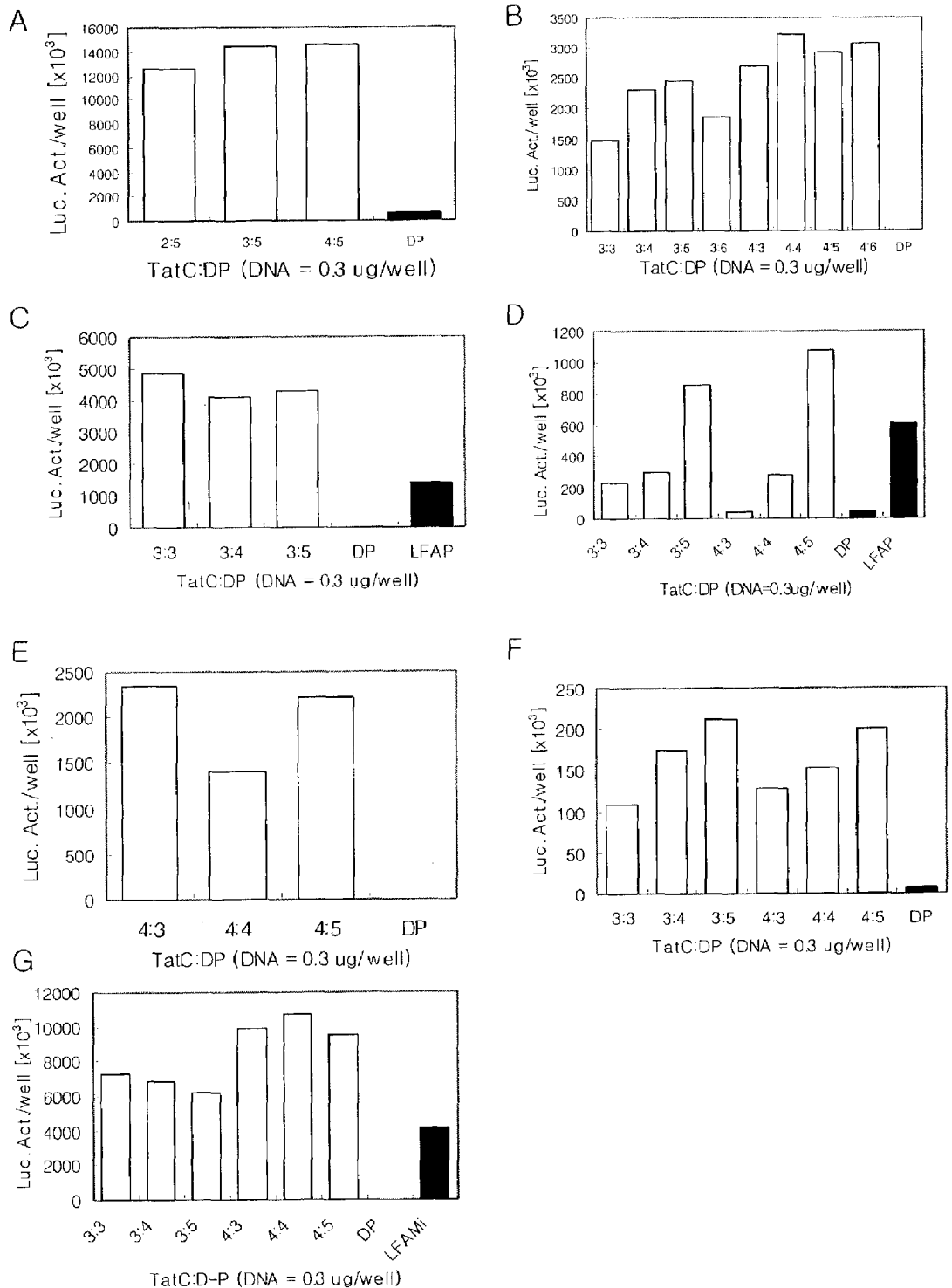
FIGS. 6A-6G show transfection efficiency in different human cells using the triple complex of TatC peptide/DNA/DP liposomes. The mixing ratios between the Tat C peptide and DP liposomes is shown. DNA ratio is kept at 1 (0.3 ug). A: 293 cells; B: HT-29 cells; C: MCF-7 cells; D: A549 cells; E: NC1-H1299 cells; F: WI-38VA13 cells; and G: Hep3B cells.
Figure 7:
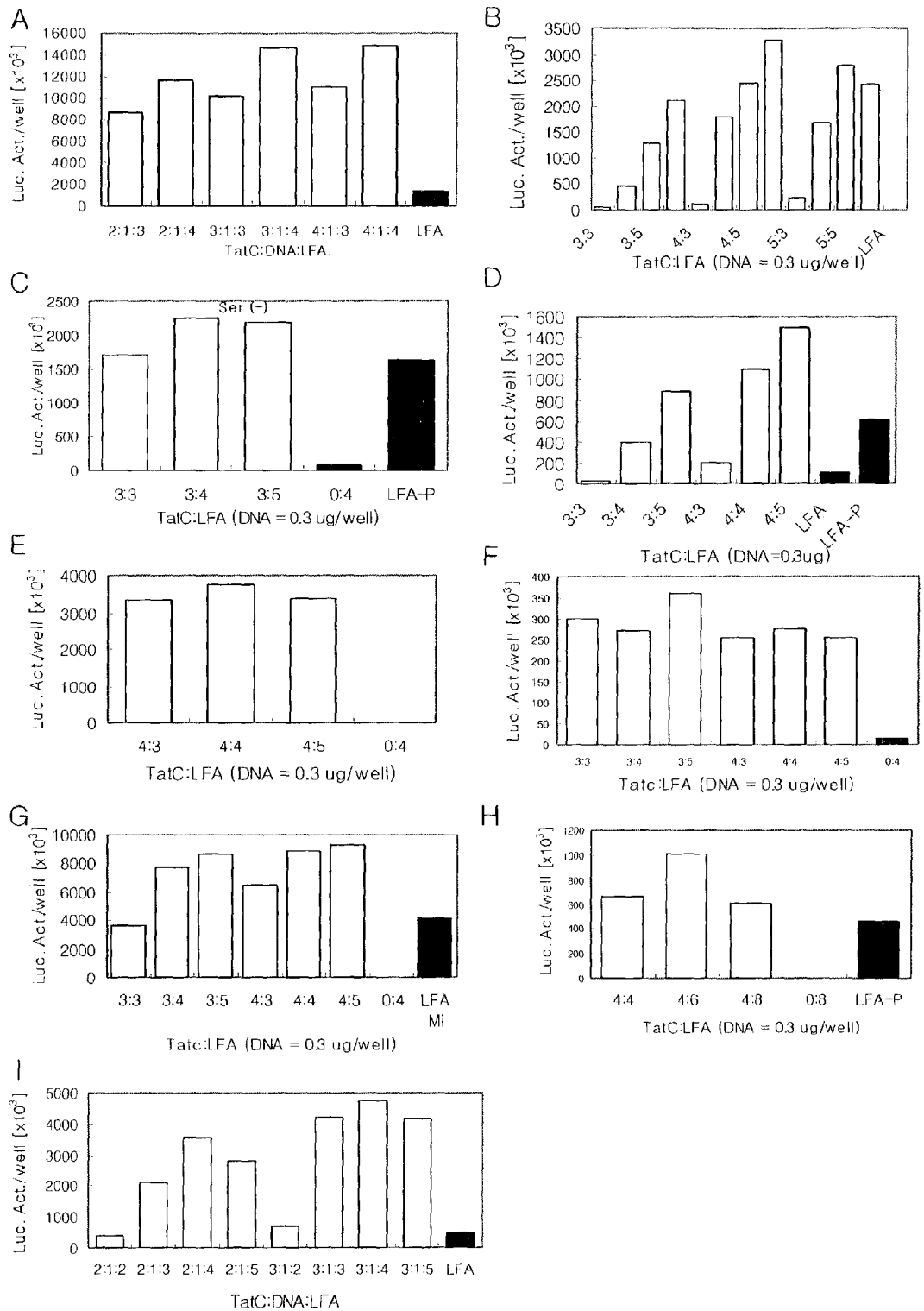
FIGS. 7A-7I show transfection efficiency in different human cell lines using the triple complex of TatC peptide/DNA/LFA liposomes. The mixing ratios between the TatC peptide and DP liposomes is shown. DNA ratio is kept at 1 (0.3 ug). A: 293 cells; B: HT-29 cells; C: MCF-7 cells; D: A549 cells; E: NC1-HI299 cells; F: WI-38VA13 cells; G: Hep3B cells; H: HL-60; and I: HepG2

Transfection Efficiency of the Triple Complex of Peptide/DNA/Liposomes in Different Cell Lines Transfection efficiency was studied using differing ratios of the three components of the triple complexes, in 9 different cell lines (293, HT-29, HL-60, MCF-7, A549, NC1-H1299, WI-38VA13, HepG2 and Hep3B cells). The triple complexes were first formed in various ratios by changing the ratio between the TatC peptide of the present invention and DNA (pcDNA3-luc. vector). Transfected cells were assayed for luciferase activity using the same procedure described in Example 3.1. The triple complex of the TatC peptide/DNA/DP showed remarkably higher luciferase activity than DP liposomes alone. Analogous results were obtained with the triple complex of the TatC peptide/DNA/LFA (FIG. 6 and FIG. 7). These results demonstrate that the peptide of the present invention can be used to deliver target DNA into a wide spectrum of cells.

Example 8

Efficiency of Cellular Uptake for FITC-Labeled Oligonucleotide

Figure 8:
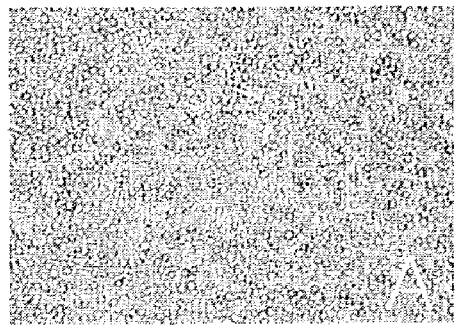
FIGS. 8A-8D show transfection efficiency for FITC-labeled oligonucleotides using the triple complex in WRT7/P2 cells. Transfected WRT7/P2 cells were observed using a light microscope. A: WRT7/P2 cells without transfection; B: Treatment of the triple complex of TatC peptide/FITC-labeled oligonucleotide/LFA liposomes; C: Treatment of the dual complex of the FITC-labeled oligonucleotides/LFA liposomes (without the TatC peptides); D: Treatment of the FITC-labeled oligonucleotides alone.
Figure 8:
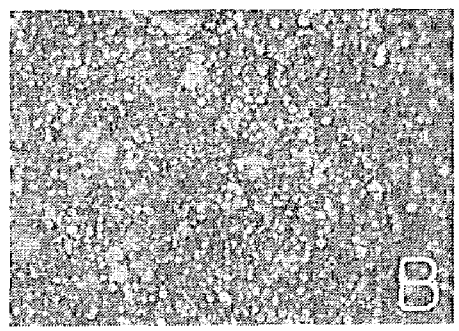
Figure 8:
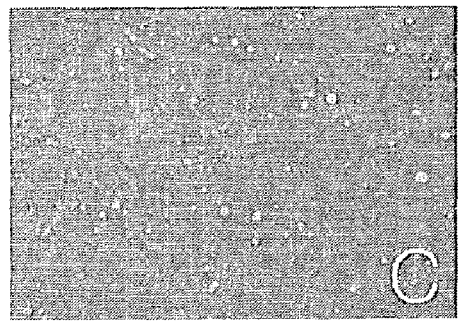
Figure 8:
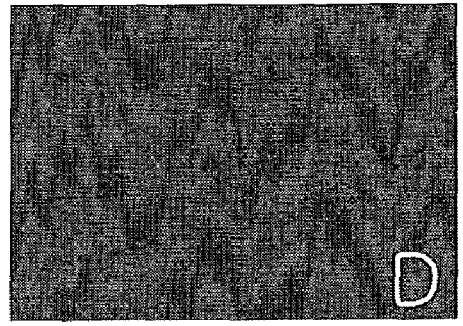

Next, transfection efficiency of nucleic acid by the triple complex was tested for oligonucleotides labeled with FITC at both ends. Oligonucleotides were complexed with the TatC peptide and LFA liposomes and were transfected to a rat monocytic cell line, WRT7/P2. The transfected cells were then assayed for FITC-fluorescence. We observed that cellular uptake of the oligonucleotides with the TatC peptide/DNA/LFA triple complex was much higher than delivered with LFA liposomes alone (FIG. 8). These results suggest that the delivery method using the triple complex of the present invention is an effective means for intracellular delivery of oligonucleotides, such as AS-oligos, decoy molecules, ribozyme, etc. Therefore, the TatC peptide delivery system of the present invention may be effectively utilized for efficient delivery into cells regardless of the types of DNA to be delivered.

Example 9

Delivery Efficiency of Modified TatC Peptides

Example 9.1

Preparation and Cellular Uptake of Modified TatC Peptides

The TatC peptide shown in Example 2.1 was modified with RGD amino acid sequence at both N-and C-termini. This type of modification is routine to the practitioner in the art. The modified peptide molecule was designated as "RGD-TatC-RGD" peptide designated as SEQ ID NO:3.

Another type of peptide molecule was synthesized by adding two RGD sequences in succession to the C-terminus of the TatC peptide. The peptide was named as "TatC-RGD-RGD" having SEQ ID NO:4. Triple complexes of peptide/DNA/liposomes were then formed with the two types of modified peptides. pcDNA3 vector containing the luciferase gene and DP liposomes were used to form the triple complexes. Both K562 cells and HeLa cells were transfected with the vector DNA complexed with peptide and DP liposomes in a ratio of about 1:4:4 (w/w/w), respectively. Luciferase activity was measured for each transfected cells as described in Example 3.1.

Figure 9:
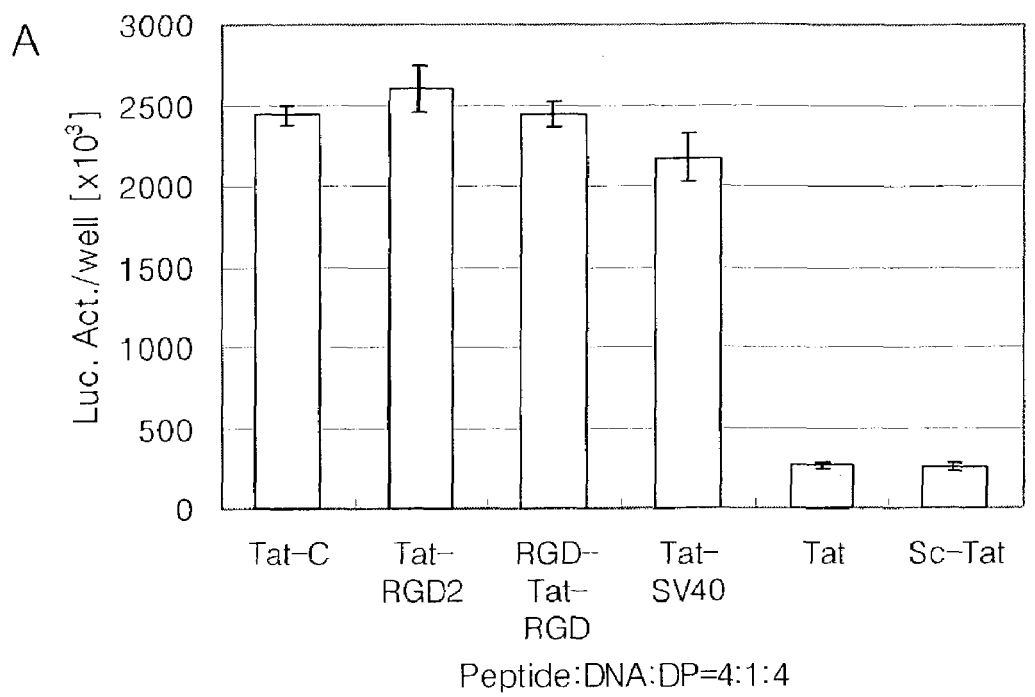
FIGS. 9A-9B show luciferase activities for various peptides. A: luciferase activity in HeLa cells for various modified peptides. B: luciferase activity in K562 cells for various modified peptides.
Figure 9:
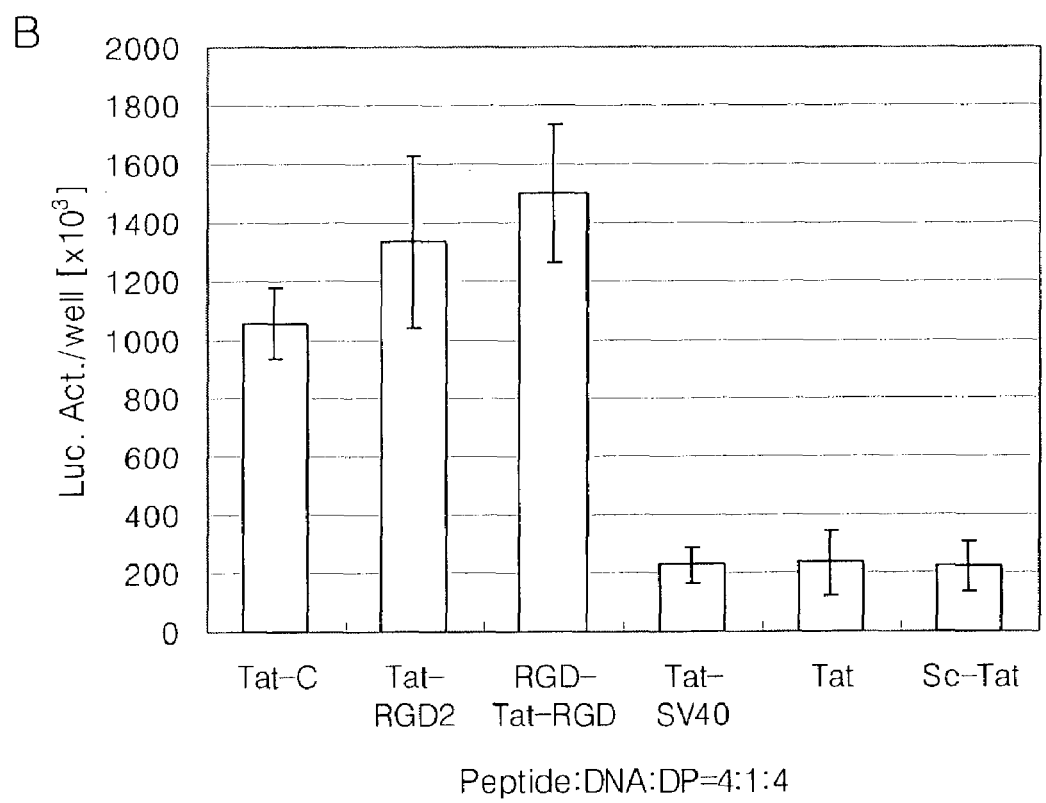

In HeLa cells, the TatC peptide, RGD-TatC-RGD peptide, and TatC-RGD-RGD peptide of the present invention showed markedly higher luciferase activity as compared to two controls, that is the Tat peptide (SEQ ID NO:6) without any modification or a scrambled peptide with modification (Sc-Tat peptide designated as SEQ ID NO:5) (FIG. 9A). These modified peptides showed a similar pattern of enhanced delivery in K562 cells as well (FIG. 9B).

In particular, both the Tat peptide containing the NLS (nuclear localization signal) motif SEQ ID NO:6) and the Sc-Tat peptide (SEQ ID NO:5) with random disturbance of the NLS motif were comparably low when compared to the Tat peptide with modifications. These results indicate that the improved delivery was achieved not only by the NLS itself, but by the modifications of the Tat peptide of the present invention.

Example 9.2

Analysis of GFP Gene Expression Mediated by the Triple Complex (TatC/DNA/Liposomes)

Figure 10:
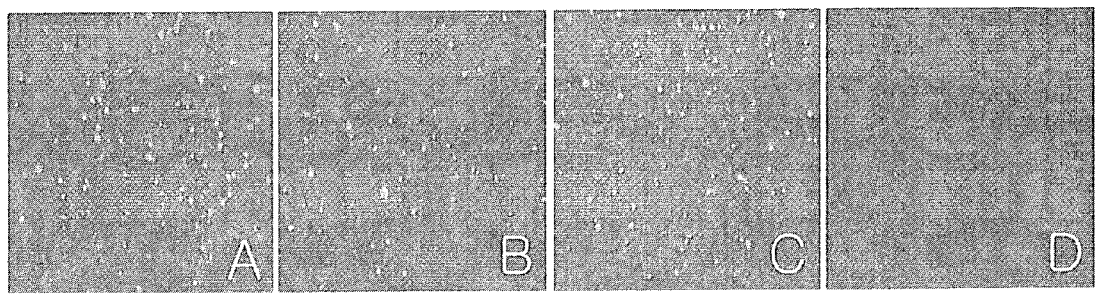
FIGS. 10A-10D show transfection efficiency in HL-60 cells. GFP gene expression is seen using various modified peptides. A: Treatment with the TatC peptide; B: Treatment with the TatC-RGD-RGD peptide; C: Treatment with the RGD-TatC-RGD peptide; and D: Treatment of the scrambled Tat peptide (negative control).
Figure 11:
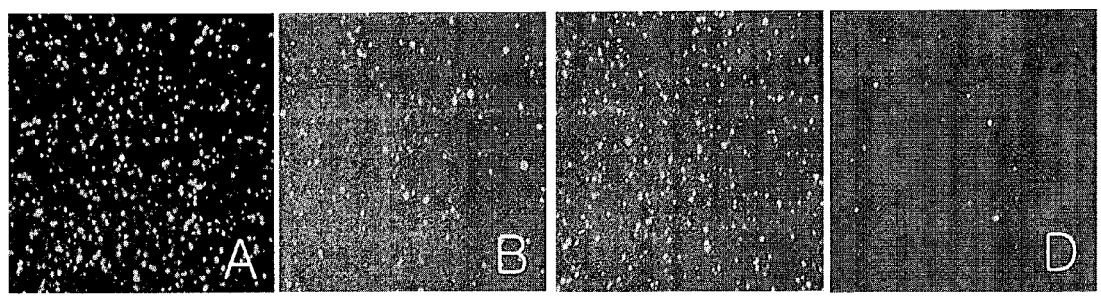
FIGS. 11A-11D show transfection efficiency in K562 cells. GFP gene expression is seen using various modified peptides. A: Treatment of the TatC peptide; B: Treatment of the TatC-RGD-RGD peptide; C: Treatment of the RGD-TatC-RGD peptide; D: Treatment of scrambled Tat peptide (negative control).

The efficiency of in vitro gene delivery was confirmed using liposomes complexed with modified Tat peptides including TatC and other derivatives described above. Firstly, as described in the aforementioned description (Example 3.1), the triple complex of peptide/DNA/DP liposomes was formulated and was then transfected into HL-60 and K562 cells. GFP expression was observed under a fluorescent microscope (Leica, Germany) after washing the transfectants twice in PBS buffer. As a result, triple complexes containing the peptides of the present invention showed 5 to 7 fold higher GFP expression as compared to the Sc-Tat peptide in HL-60 cells as described in FIG. 10. Likewise, GFP expression was shown to be higher when used with Tat peptides as compared with control peptides. These results are in good agreement with the results obtained with luciferase 562 cells shown in Example 9.1) (FIG. 11).

Example 10

Efficiency of Viral Production by Peptide-Mediated Co-Transfection

To analyze co-transfection efficiency using the peptide delivery method of present invention, the triple complex of peptide/DNA/liposomes was formulated in which three different plasmids (ACP-luciferase, pXX2, and pXX6) were used for production of recombinant adeno-associated virus (rAAV). The three plasmids required for rAAV production are shown in TABLE 3.

TABLE 3

| Plasmid DNA | Specification | Obtained from |
|---|---|---|
| ACP-luciferase | Containing ITR at the end of insert and the CMV promotor, the luciferase gene, and the BGH poly(A) signal sequence | Dr. D. K. Kim of Sungkyunkwan University, School of medicine |
| XX2 | Containing the cap ORF and The rep ORF | The University of North Carolina at Chapel Hill |
| XX6 | Containing adenovirus E1A, E1B, E2A, E4 and VA genes | |

Example 10.1

Measurement of Luciferase Activity Following Co-Transfection $7 \times 10^5$ cells/well of 293 cells, were seeded in each well of a 6-well plate 24 h prior to transfection, and incubated further in a humidified incubator at 5% $CO_2$ and 37° C. Thereafter, the TatC peptide (Example 2.1) was complexed with a mixture of plasmids (ACP-Luc:pXX2:pXX6=1:1:3 (w/w)) at the ratio of 3:1, 4:1, and 5:1, and incubated for 5 minutes at room temperature. The complex of plasmids and TatC was added with 5 fold of DP liposomes (w/w), and incubated further for 10 min at room temperature. The triple complex was then added into 293 cells after wash with OPTI-MEM medium without serum. 293 cells were incubated with the triple complex for 6 hours in a $CO_2$ incubator, and then added with 1 ml EMEM containing 20% FBS in each well. The cells were further incubated for 24 hours. A transfection method using calcium phosphate was used as a control method to compare transfection efficiency.

Figure 12:
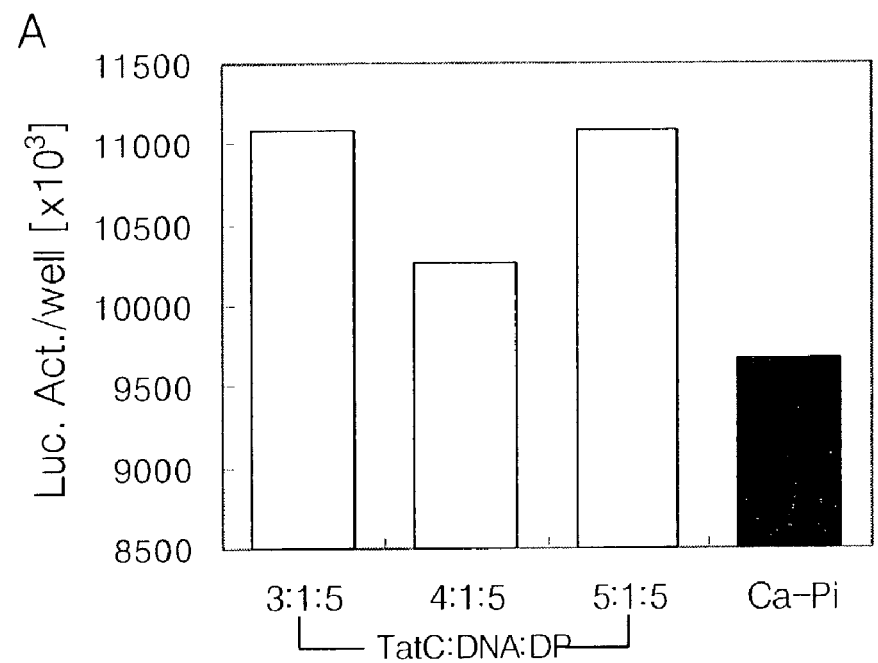
FIGS. 12A-12B show transfection efficiency. A: transfection efficiency in luciferase activity when cells are co-transfected with three kinds of plasmid DNA is measured. The transfection method using calcium-phosphate precipitation is employed as a transfection control. B: luciferase activity by co-infection of recombinant AAV and wild type adenovirus to HeLaRC32 cells. Recombinant AAV is produced by co-transfection of three kinds of plasmid DNA into HeLaRC32 cells. Recombinant AAV content is measured by luciferase activity after co-infection of recombinant AAV and wild type adenovirus. The method of calcium-phosphate precipitation as a negative control was also employed for co-transfection of the three kinds of plasmid DNA into HeLaRC32 cells.
Figure 12:
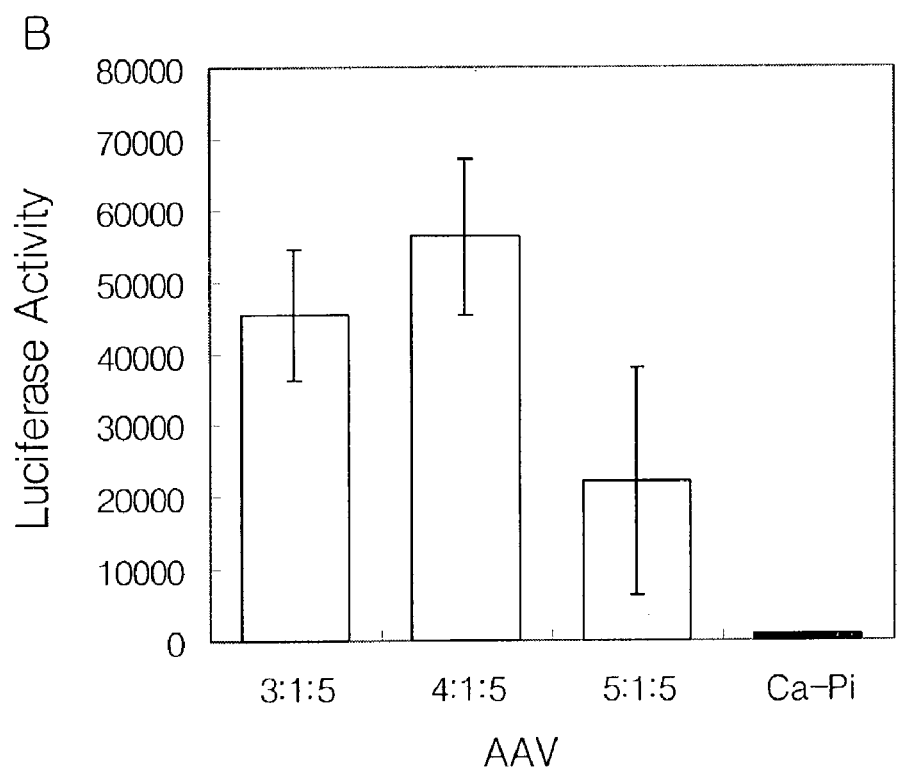

As a result, as described in FIG. 12A, luciferase activity was higher than the Ca-Pi method when a complex of peptide/DNA/liposomes of the present invention was used.

Example 10.2

Examination of Gene Delivery Efficiency by Quantification of rAAV Production

Luciferase is also expressed when cells are transfected with pACP-Luc alone among the plasmids mentioned in FIG. 12A. However, co-transfection of the three plasmids is necessary for generation of rAAV particles. In addition, migration of the three plasmids into the nucleus is essential for expression of genes in the three plasmids. Consequently, rAAV production can be measured indirectly by examination of luciferase activity in transfectants.

Transfection was first performed as mentioned in Example 10.1 for 72 hours in 293 cells. Cells were then harvested and lysed by repeated cycles of freezing and thawing. Thereafter, HeLaRC32 cells were co-infected with harvested cell supernatant and wild type adenovirus at 50 MOI. Luciferase activity was measured after 24 hours. At the same time, control cell supernatant was prepared by the calcium-phosphate method. The supernatants were then used for infection to HeLaRC32 cells together with wild type adenovirus. As a result, as illustrated in FIG. 12B, when transfection was performed with the peptide/DNA/liposomes triple complex at a ratio of approximately 4:1:5, luciferase activity was found to be higher than calcium phosphate method. This demonstrates that all three tested plasmids were efficiently translocated into cells and resulted in efficient production of rAAV because of high transfection efficiency mediated by the peptide gene delivery method of the present invention. Hence, the present invention provides an effective method of delivering more than one DNA into cells simultaneously.

Example 11

Figure 13:
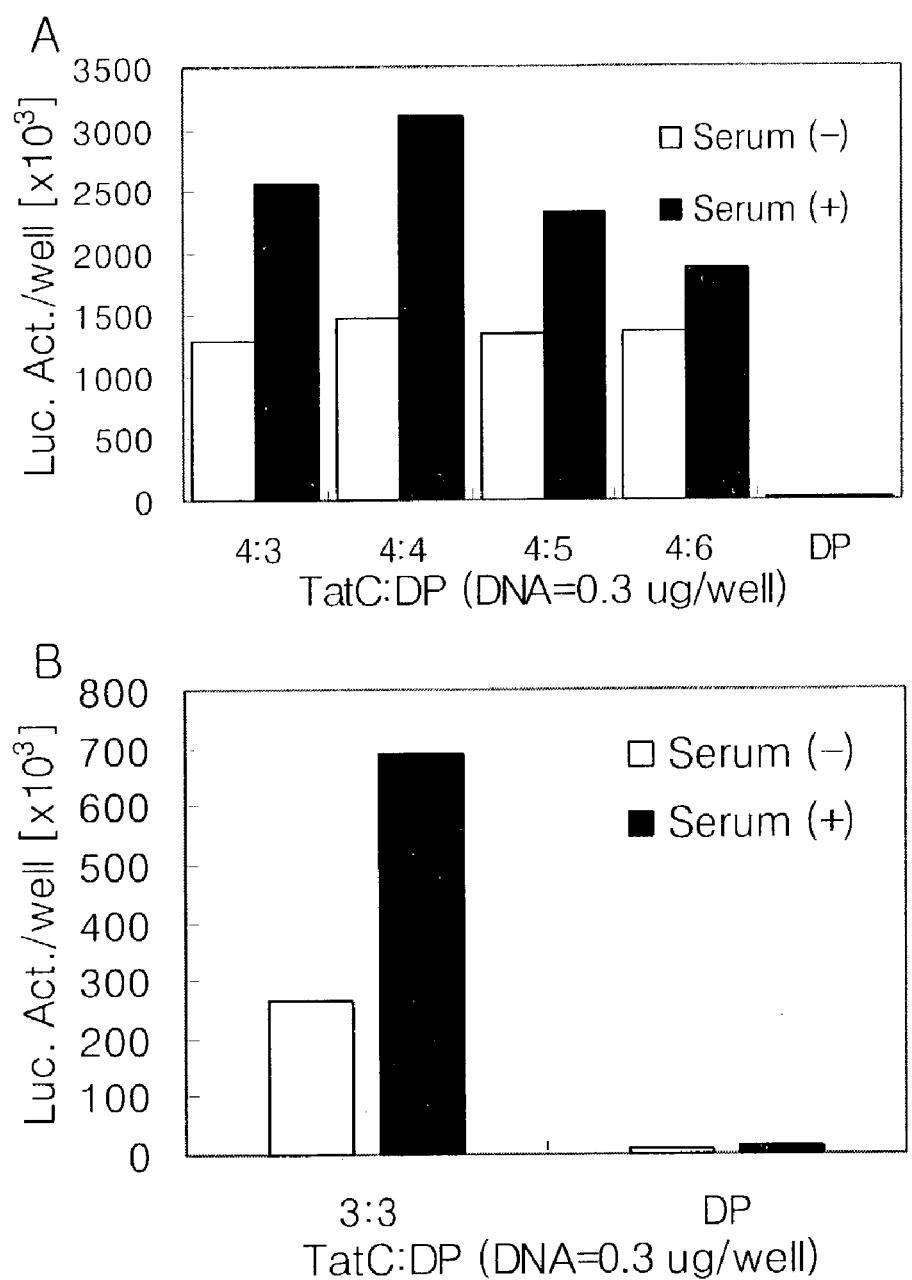
FIGS. 13A-13B show luciferase activity to demonstrate the effect of serum on transfection efficiency. A: Transfection in HeLa cells; and B: Transfection in K562 cells.
Figure 14:
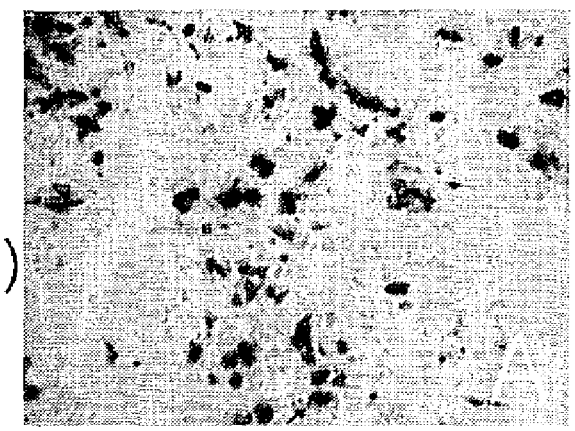
FIGS. 14A-14C show luciferase activity to demonstrate the effect of serum on transfection efficiency into HeLa cells using plasmid DNA containing the GFP gene. A: Transfection in a medium without serum; B: Transfection in a medium containing serum (10% FBS); and C: Control transfection without using peptides (DNA-liposome complex, with 10% FBS)
Figure 14:
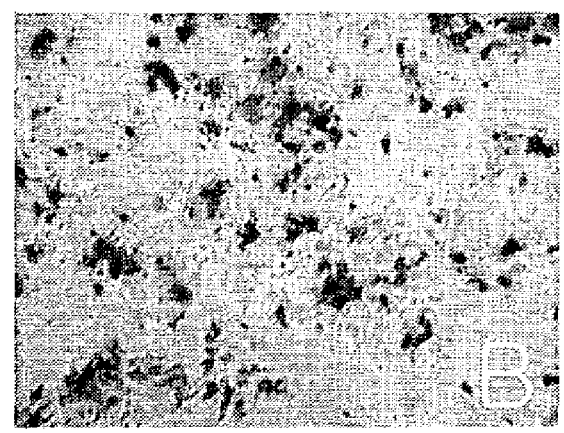
Figure 14:
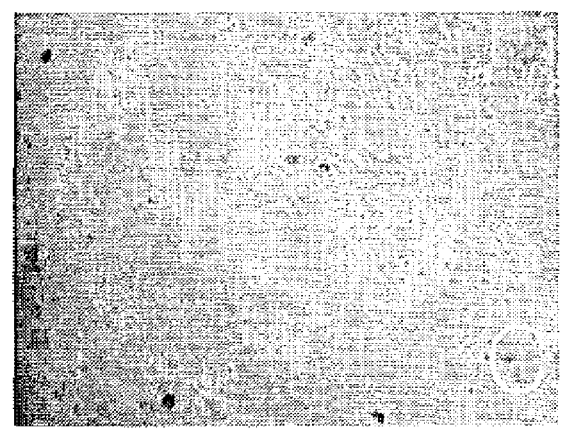
Figure 15:
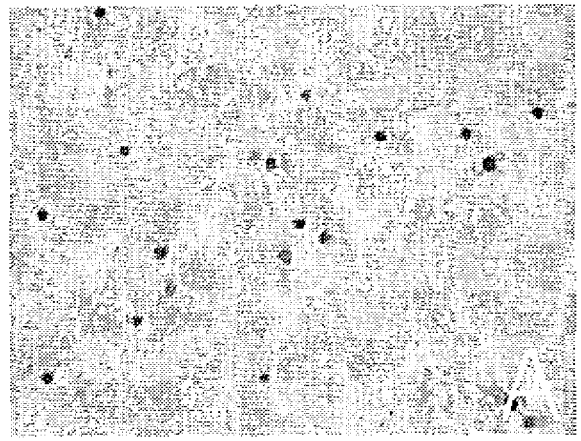
FIGS. 15A-15C show luciferase activity to demonstrate the effect of serum on transfection efficiency into K562 cells using plasmid DNA containing GFP gene. A: Transfection in a medium without serum; B: Transfection in a medium containing serum (10% FBS); and C: Control transfection without using peptides (DNA-liposome complex, with 10% FBS)
Figure 15:
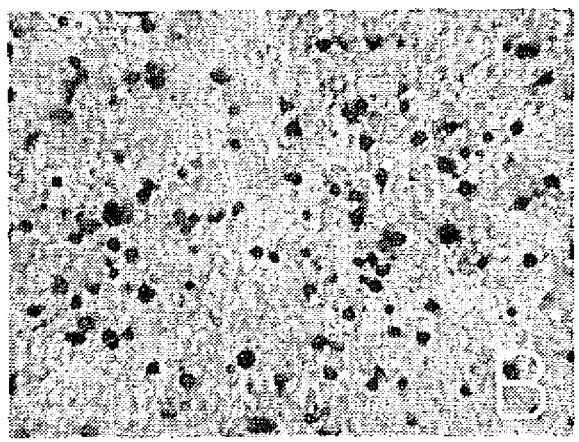
Figure 15:
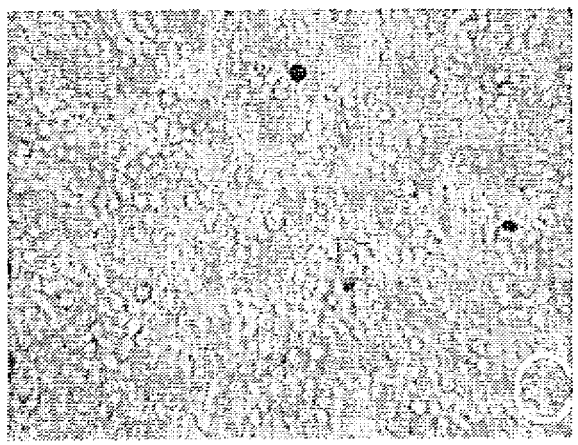

Examination of Transfection Efficiency Using Peptide in the Presence or Absence of Serum To examine transfection efficiency in the presence or absence of serum, the TatC/DNA(pcDNA3-luc)/DP liposomes triple complex of the present invention was transfected into HeLa and K562 cells in a medium with or without 10% FBS (FIG. 13A and B). A complex of DNA and liposomes was used as a negative control. As a result, as shown in FIG. 13, luciferase activity obtained with the TatC/DNA/liposome complex was higher in medium containing serum as compared to medium without serum. Furthermore, the results shown in FIGS. 14 and 15 using the 13-galactosidase reporter gene were consistent with those shown in FIG. 13. These results demonstrate that the peptide mediated DNA delivery of the present invention may be useful both in vitro and iii vivo.

Example 12

Examination of Delivery Efficiency of the Triple Complex Containing the TatC Peptide In Vivo To test the transfection efficiency of the peptide/DNA/liposomes triple complex in vivo, the following experiment was performed. Male Sprague-Dawley (SD) rats (Hamamatsu, Shizuoka, Japan) were supplied from SLC and were housed in groups of 6 with free access to standard chow and water. Male SD rats, weighing 200-250 g, were used in these experiments. After anesthesia by the intraperitoneal injection of pentobarbital (5 mg/100 g body weight), the left kidney was exposed via an abdominal midline incision. Rats were subjected to ureteral ligation proximal to the left kidney, which was followed by retrograde injection of the triple complex (TatC: DNA: DP=4:1:4) using a 24 gauge catheter syringe. Kidneys were harvested 24 hours after injection of the triple complex. and embedded in a Tissue-Tek™ OCT compound (Miles, Elkhart, Ill.) under liquid nitrogen. Tissue blocks of the perfusion-fixed kidney with 4% paraformaldehyde were cryosectioned to 10 µm thickness and mounted on Poly-Prep™ slides (Sigma, St. Louise, Mo.). After dissection of individual kidneys, kidney sections were fixed with 0.05% glutaraldehyde in PBS by perfusion for 15 min, and incubated in X-gal solution (1.5 mM potassium ferricyanide, 1.5 mM potassium ferrocyanide, and 1% X-gal) at 37° C. for 4 h. Tissue sections of 4 µm were counterstained with hematoxylin and examined using a microscope at 400 fold magnification.

Figure 16:
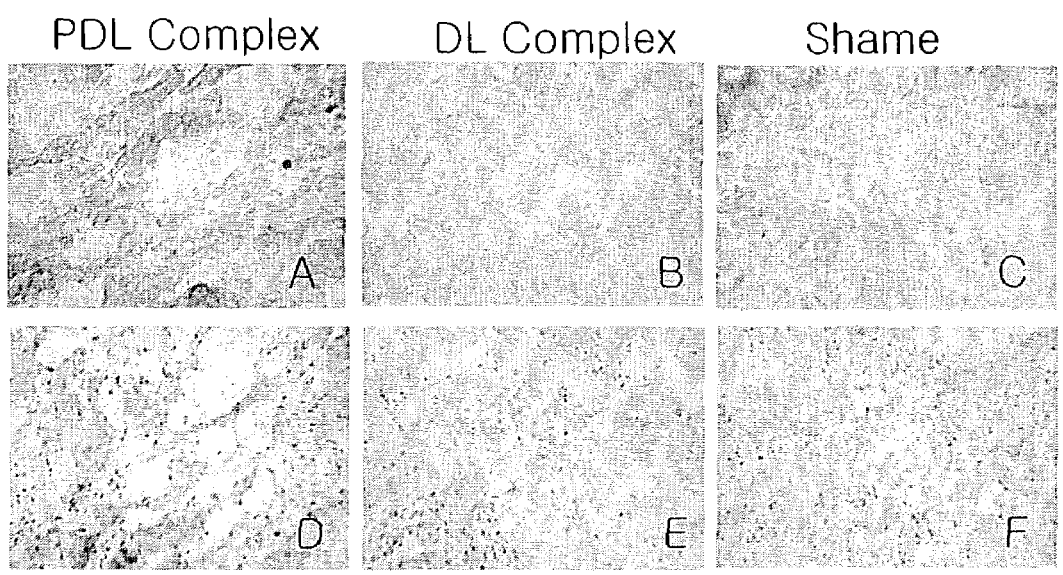
FIGS. 16A-16F show transfection efficiency in the kidney of SD rats by using the triple complex of the TatC peptide/DNA/liposomes. Plasmid DNA contained LacZ gene. The complex was infused through the ureteric route of SD rats. After 48 h, kidneys were extracted and subjected to frozen-section. Sections of 10 m thickness were washed with PBS and fixed with 0.05% glutaraldehyde. Slides were immersed in the X-gal solution overnight and were counterstained with hematoxylin (D~E). (Magnification, 400×). The triple complex: TatC peptide/DNA/liposomes (PDL complex); and the dual complex: DNA/liposomes.

As illustrated in FIG. 16, expression of the β-galactosidase gene was observed only in the group treated with the complex composed of TatC/DNA/liposomes but not in the group treated with either DNA/liposome or DNA alone. Hence, the triple complex of TatC/DNA/liposomes provides a significant benefit for gene delivery both in vitro and in vivo.

UTILITY OF THE INVENTION

As mentioned above, inventors of the present invention have made structurally and functionally effective Tat-derived peptides, containing a basic 12 amino acid sequence which has a function in nuclear localization, The inventors designed peptides with amino acid modifications at the N-terminal and/or C-terminal ends of the basic amino acids sequence mentioned above. The peptides of the present invention will be of use in overcoming limitations of DNA delivery using cationic liposomes. The triple complex using the TatC peptide can be easily formulated for large scale production, which is essential for industrial applications. Further, the TatC peptide can also be used for co-transfection of more than one plasmid into cells at high transfection efficiency both in vivo and in vitro. Therefore, this invention can be of use as a delivery tool for gene therapy.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

The invention claimed is:

1. A transfection effective carrier polypeptide comprising parts $A_n$-B-$A_n$, wherein part B is at least 70% homologous to SEQ ID NO:2, and A represents Arg-Gly-Asp, and n represents a number from 0 to 2, wherein parts A and B are covalently linked, and wherein if n is 0 at N-terminus, then n is 1 or 2 at C-terminal, and if n is 0 at C-terminus, then n is 1 or 2 at the N-terminus.

2. The polypeptide according to claim 1, wherein part B has at least 80% homology to SEQ ID NO:2.

3. The polypeptide according to claim 1, wherein the polypeptide is about 30 amino acids in length.

4. The polypeptide according to claim 1, wherein the polypeptide is about 10 to 20 amino acids in length.

5. The polypeptide according to claim 1, wherein the polypeptide is represented by SEQ ID NO:3.

6. The polypeptide according to claim 1, wherein the polypeptide is represented by SEQ ID NO:4.

7. A method of inserting at least one nucleic acid into a cell, comprising contacting the cell with a composition comprising the nucleic acid and the polypeptide according to claim 1.

8. The method according to claim 7, wherein the composition comprises a nucleic acid delivery carrier.

9. The method according to claim 8, wherein the nucleic acid delivery carrier is a cationic liposome.

10. The method according to claim 7, wherein the composition is mixed before contacting the cell.

11. The method according to claim 7, wherein the nucleic acid is an oligonucleotide with a size range from 10 to 1000 bases.

12. The method according to claim 7, wherein the nucleic acid is a plasmid vector.

13. The method according to claim 7, wherein the nucleic acid is a single stranded DNA having a length from about 300 to about 20,000 bases.

14. The method according to claim 9, wherein the cationic liposome is DOTAP-DOPE.

15. The method according to claim 8, wherein the ratio of polypeptide, nucleic acid and liposome is about 1-10:1:1-10 (w/w/w).

16. The method according to claim 14, wherein the liposome is DOTAP-DOPE (1:1).

17. The method according to claim 16, wherein the ratio of polypeptide, nucleic acid and DOTAP:DOPE (1:1) is about 3-5:1:3-6 (w/w/w).

18. An in vitro transfection system comprising the polypeptide according to claim 1 and a cationic liposome.

19. The transfection system according to claim 18, wherein said cationic liposome is DOTAP-DOPE (1:1).

* * * * *

SEQUENCE LISTING

```
<160> NUMBER OF SEQ ID NOS: 11

<210> SEQ ID NO 1
<211> LENGTH: 25
<212> TYPE: PRT
<213> ORGANISM: artificial
<220> FEATURE:
<223> OTHER INFORMATION: RGD-RGD-TatC-RGD-RGD

<400> SEQUENCE: 1

Arg Gly Asp Arg Gly Asp Arg Lys Lys Arg Arg Gln Arg Arg Pro
1               5                   10                  15

Pro Gln Cys Arg Gly Asp Arg Gly Asp
            20                  25

<210> SEQ ID NO 2
<211> LENGTH: 13
<212> TYPE: PRT
<213> ORGANISM: Artificial
<220> FEATURE:
<223> OTHER INFORMATION: TatC

<400> SEQUENCE: 2

Arg Lys Lys Arg Arg Gln Arg Arg Arg Pro Pro Gln Cys
1               5                   10

<210> SEQ ID NO 3
<211> LENGTH: 19
<212> TYPE: PRT
<213> ORGANISM: Artificial
<220> FEATURE:
<223> OTHER INFORMATION: RGD-TatC-RGD

<400> SEQUENCE: 3

Arg Gly Asp Arg Lys Lys Arg Arg Gln Arg Arg Arg Pro Pro Gln Cys
1               5                   10                  15

Arg Gly Asp

<210> SEQ ID NO 4
<211> LENGTH: 19
<212> TYPE: PRT
<213> ORGANISM: Artificial
<220> FEATURE:
<223> OTHER INFORMATION: TatC-RGD-RGD

<400> SEQUENCE: 4

Arg Lys Lys Arg Arg Gln Arg Arg Arg Pro Pro Gln Cys Arg Gly Asp
1               5                   10                  15

Arg Gly Asp
```

```
<210> SEQ ID NO 5
<211> LENGTH: 12
<212> TYPE: PRT
<213> ORGANISM: Artificial
<220> FEATURE:
<223> OTHER INFORMATION: Scrambled Tat(Sc-Tat)

<400> SEQUENCE: 5

Arg Arg Lys Arg Gln Arg Lys Arg Arg Pro Gln Pro
1               5                   10

<210> SEQ ID NO 6
<211> LENGTH: 12
<212> TYPE: PRT
<213> ORGANISM: Artificial
<220> FEATURE:
<223> OTHER INFORMATION: Tat

<400> SEQUENCE: 6

Arg Lys Lys Arg Arg Gln Arg Arg Arg Pro Pro Gln
1               5                   10

<210> SEQ ID NO 7
<211> LENGTH: 16
<212> TYPE: PRT
<213> ORGANISM: artificial
<220> FEATURE:
<223> OTHER INFORMATION: TatC-RGD

<400> SEQUENCE: 7

Arg Lys Lys Arg Arg Gln Arg Arg Arg Pro Pro Gln Cys Arg Gly Asp
1               5                   10                  15

<210> SEQ ID NO 8
<211> LENGTH: 16
<212> TYPE: PRT
<213> ORGANISM: artificial
<220> FEATURE:
<223> OTHER INFORMATION: RGD-TatC

<400> SEQUENCE: 8

Arg Gly Asp Arg Lys Lys Arg Arg Gln Arg Arg Arg Pro Pro Gln Cys
1               5                   10                  15

<210> SEQ ID NO 9
<211> LENGTH: 22
<212> TYPE: PRT
<213> ORGANISM: artificial
<220> FEATURE:
<223> OTHER INFORMATION: RGD-TatC-RGD-RGD

<400> SEQUENCE: 9

Arg Gly Asp Arg Lys Lys Arg Arg Gln Arg Arg Arg Pro Pro Gln Cys
1               5                   10                  15

Arg Gly Asp Arg Gly Asp
            20

<210> SEQ ID NO 10
<211> LENGTH: 19
<212> TYPE: PRT
<213> ORGANISM: artificial
<220> FEATURE:
<223> OTHER INFORMATION: RGD-RGD-TatC
```

-continued

```
<400> SEQUENCE: 10

Arg Gly Asp Arg Gly Asp Arg Lys Lys Arg Arg Gln Arg Arg Arg Pro
1               5                   10                  15

Pro Gln Cys

<210> SEQ ID NO 11
<211> LENGTH: 22
<212> TYPE: PRT
<213> ORGANISM: artificial
<220> FEATURE:
<223> OTHER INFORMATION: RGD-RGD-TatC-RGD

<400> SEQUENCE: 11

Arg Gly Asp Arg Gly Asp Arg Lys Lys Arg Arg Gln Arg Arg Arg Pro
1               5                   10                  15

Pro Gln Cys Arg Gly Asp
            20
```